United States Patent
Altobelli et al.

(10) Patent No.: US 8,882,852 B2
(45) Date of Patent: Nov. 11, 2014

(54) DYNAMIC SUPPORT APPARATUS AND SYSTEM

(75) Inventors: David E. Altobelli, Hollis, NH (US); N. Christopher Perry, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 13/323,094

(22) Filed: Dec. 12, 2011

(65) Prior Publication Data

US 2012/0101598 A1    Apr. 26, 2012

Related U.S. Application Data

(63) Continuation of application No. 12/706,340, filed on Feb. 16, 2010, now Pat. No. 8,074,559, which is a continuation-in-part of application No. 12/026,971, filed on Feb. 6, 2008.

(60) Provisional application No. 61/168,793, filed on Apr. 13, 2009, provisional application No. 60/899,835, filed on Feb. 6, 2007.

(51) Int. Cl.
| | |
|---|---|
| *A61F 5/00* | (2006.01) |
| *A61F 2/54* | (2006.01) |
| *A61F 2/80* | (2006.01) |
| *A61F 5/01* | (2006.01) |
| *A61F 7/00* | (2006.01) |

(52) U.S. Cl.
CPC ........... *A61F 5/012* (2013.01); *A61F 2007/006* (2013.01)
USPC ................... 623/58; 602/13; 602/14; 623/36; 623/37

(58) Field of Classification Search
CPC .............................. A61F 2/7812; A61F 2/7843
USPC ............................................................. 623/58
See application file for complete search history.

(56) References Cited

U.S. PATENT DOCUMENTS

| | | | |
|---|---|---|---|
| 975,029 | A | 11/1910 | Galvin |
| 2,350,339 | A | 6/1944 | Costa |

(Continued)

FOREIGN PATENT DOCUMENTS

| | | | |
|---|---|---|---|
| DE | 19624215 C1 | 4/1997 | |
| EP | 1159940 A2 | 12/2001 | |

(Continued)

OTHER PUBLICATIONS

Partial International Search Report from corresponding international appln. No. PCT/US2011/041345 dated Mar. 5, 2012 (22 pages).

(Continued)

*Primary Examiner* — David Isabella
*Assistant Examiner* — Jacqueline Woznicki
(74) *Attorney, Agent, or Firm* — McCormick, Paulding & Huber LLP

(57) ABSTRACT

A dynamic support apparatus having a frame, a dynamic interface, a temperature control mechanism, and a control system. The dynamic interface is capable of changing its geometry and is disposed on the top surface of the frame. The control system is operably connected to the dynamic interface and controls the changing geometry of the dynamic interface. There is also a temperature control mechanism disposed on the top surface of the frame for maintaining a comfortable temperature and moisture environment between the apparatus and the user's body.

21 Claims, 25 Drawing Sheets

(56) References Cited

U.S. PATENT DOCUMENTS

| | | | |
|---|---|---|---|
| 2,408,880 A | 10/1946 | Rebers |
| 2,516,791 A | 7/1950 | Motis et al. |
| 3,745,998 A | 7/1973 | Rose |
| 3,779,654 A | 12/1973 | Horne |
| 3,987,498 A | 10/1976 | Mason |
| 4,030,141 A | 6/1977 | Graupe |
| 4,068,763 A | 1/1978 | Fletcher et al. |
| 4,209,860 A | 7/1980 | Graupe |
| 4,253,449 A | 3/1981 | Arkans et al. |
| 4,521,924 A | 6/1985 | Jacobsen et al. |
| 4,628,765 A | 12/1986 | Dien et al. |
| 4,657,003 A | 4/1987 | Wirtz |
| 4,743,264 A | 5/1988 | Sherva-Parker |
| 4,840,634 A | 6/1989 | Muller et al. |
| 4,842,608 A | 6/1989 | Marx et al. |
| 5,018,513 A | 5/1991 | Charles |
| 5,108,456 A | 4/1992 | Coonan, III |
| 5,201,772 A | 4/1993 | Maxwell |
| 5,611,774 A | 3/1997 | Postelmans |
| 5,673,367 A | 9/1997 | Buckley |
| 6,171,239 B1 | 1/2001 | Humphrey |
| 6,301,964 B1 | 10/2001 | Fyfe et al. |
| 6,350,211 B1 | 2/2002 | Kolmar |
| 6,361,570 B1 | 3/2002 | Gow |
| 6,454,513 B1 | 9/2002 | Friederichs et al. |
| 6,896,704 B1 | 5/2005 | Higuchi et al. |
| 7,001,434 B2 | 2/2006 | Van De Veen |
| 7,144,430 B2 | 12/2006 | Archer et al. |
| 7,744,551 B2 | 6/2010 | Pick et al. |
| 7,837,474 B1 | 11/2010 | Nuccio-Youngs |
| 8,257,090 B1 | 9/2012 | Nuccio-Youngs |
| 2002/0099450 A1 | 7/2002 | Dean, Jr. et al. |
| 2002/0143405 A1 | 10/2002 | Davalli et al. |
| 2002/0170193 A1 | 11/2002 | Townsend et al. |
| 2003/0139783 A1 | 7/2003 | Kilgore et al. |
| 2003/0181990 A1* | 9/2003 | Phillips ........................ 623/37 |
| 2004/0054423 A1 | 3/2004 | Martin |
| 2004/0088057 A1 | 5/2004 | Bedard |
| 2005/0028392 A1 | 2/2005 | Campbell et al. |
| 2005/0066810 A1* | 3/2005 | Schulz ............................. 92/89 |
| 2005/0119777 A1 | 6/2005 | Arbogast et al. |
| 2006/0189899 A1 | 8/2006 | Flaherty et al. |
| 2006/0224247 A1 | 10/2006 | Clausen et al. |
| 2006/0282175 A1 | 12/2006 | Haines et al. |
| 2007/0186429 A1 | 8/2007 | Bonnet et al. |
| 2007/0191965 A1 | 8/2007 | Colvin et al. |
| 2007/0250179 A1 | 10/2007 | Latour |
| 2008/0009771 A1 | 1/2008 | Perry et al. |
| 2008/0045932 A1 | 2/2008 | Beau et al. |
| 2008/0215162 A1 | 9/2008 | Farnsworth et al. |
| 2008/0243266 A1 | 10/2008 | Haynes et al. |
| 2008/0252552 A1 | 10/2008 | Goebel et al. |
| 2008/0288088 A1 | 11/2008 | Langenfeld et al. |
| 2009/0000136 A1 | 1/2009 | Crampton |
| 2009/0038421 A1 | 2/2009 | Wilson et al. |
| 2009/0271000 A1 | 10/2009 | Altobelli et al. |
| 2010/0036455 A1 | 2/2010 | Sanders et al. |
| 2010/0081974 A1 | 4/2010 | Vess |
| 2010/0113994 A1 | 5/2010 | Ingimundarson et al. |
| 2011/0247321 A1 | 10/2011 | Streeter et al. |
| 2011/0257765 A1 | 10/2011 | Evans et al. |
| 2012/0123558 A1 | 5/2012 | Gill |
| 2012/0210590 A1 | 8/2012 | Ferrari |

FOREIGN PATENT DOCUMENTS

| | | |
|---|---|---|
| EP | 1675212 A1 | 6/2006 |
| EP | 1916561 A2 | 4/2008 |
| EP | 2112740 A2 | 10/2009 |
| FR | 2877227 A1 | 5/2006 |
| WO | 2004/096502 A1 | 11/2004 |
| WO | 2008/098059 A2 | 8/2008 |
| WO | 2010/033098 A1 | 3/2010 |
| WO | 2010/120403 A2 | 10/2010 |
| WO | 2010120404 A2 | 10/2010 |
| WO | 2011036473 A1 | 3/2011 |

OTHER PUBLICATIONS

Partial International Search Report from corresponding international appln. No. PCT/US2011/031797 dated Dec. 8, 2011 (4 pages).

International Search Report and Written Opinion from corresponding International Appln. No. PCT/US2009/069491 dated May 20, 2010 (13 pages).

Search Report from European Appln. No. 08729171.2 dated Aug. 29, 2011 (7 Pages).

Search Report from European Appln. No. 08729175.3 dated Aug. 29, 2011 (5 Pages).

Karoui M S et al., "Study and Design of a Loop Antenna for Application of Medical Telemetry" Industrial Technology, 2004, IEEE ICIT '04, IEEE International Conference on Hammamet, Tunsia, vol. 3, Dec. 8, 2004, pp. 1589-1595.

Yekeh K et al., "Wireless Communications for Body Implanted Medical Device" Microwave Conference, 2007, Asia-Pacific, IEEE, Piscataway, NJ, Dec. 11, 2007, pp. 1-4.

Search Report from corresponding European Appln. No. 08729167.0 dated Feb. 6, 2012 (6 pages).

Partial International Search Report from corresponding International Appln. No. PCT/US2011/041339 dated May 10, 2012 (6 pages).

International Search Report and Written Opinion from corresponding International Appln. No. PCT/US2011/031797 dated Jun. 15, 2012 (14 pages).

Zaghloul et al., "Hybrid Reflector-Array Antenna Concept," Antennas and Propagation Society International Symposium 2006 IEEE, Jul. 9-14, 2006, Virginia Polytechnic Institute and State University, Blacksburg, pp. 4311-4314, Conference Publications.

Quick Guide #3, C-Leg Patient Training Overview, Otto Bock, 2006, Training Pamphlet, pp. 1-4.

Graupe, "Control of an Artificial Upper Limb in Three Degrees of Freedom," Bulletin of Prosthetics Research, Fall 1975, pp. 25-39.

Partial International Search Report from corresponding international appln. No. PCT/US2011/041343 dated Nov. 24, 2011 (6 pages).

Preliminary Report on Patentability from corresponding International Appln. No. PCT/US2011/031797 dated Oct. 9, 2012 (8 pages).

Examination Report from corresponding European Appln. No. 10714392.7 dated Oct. 25, 2012 (4 pages).

Poulton et al., "Experience with the Intelligent Hybrid Arm Systems" from "MEC '02 TH Next Generation," Proceedings of the 2002 MyoElectric Controls/Powered Prosthetics Symposium Fredericton, New Brunswick, Canada, Aug. 21-23, 2002, Copyright University of New Brunswick, pp. 1-4.

Jacobsen et al., "Development of the Utah Artificial Arm" IEEE Transactions on Biomedical Engineering, vol. BME-29, No. 4, Apr. 1982, pp. 249-269.

Partial International Search Report from corresponding international appln. No. PCT/US2013/039081 dated Aug. 29, 2013 (6 pages).

International Search Report and Written Opinion from corresponding International Appln. No. PCT/US2013/039081 dated Oct. 29, 2013 (15 pages).

Lake, et al., Evolution of Microprocessor Based Control Systems in Upper Extremity Prosthetics, Technology and Disability IOS Press, vol. 15 (2003), pp. 63-71 (6 pages).

* cited by examiner

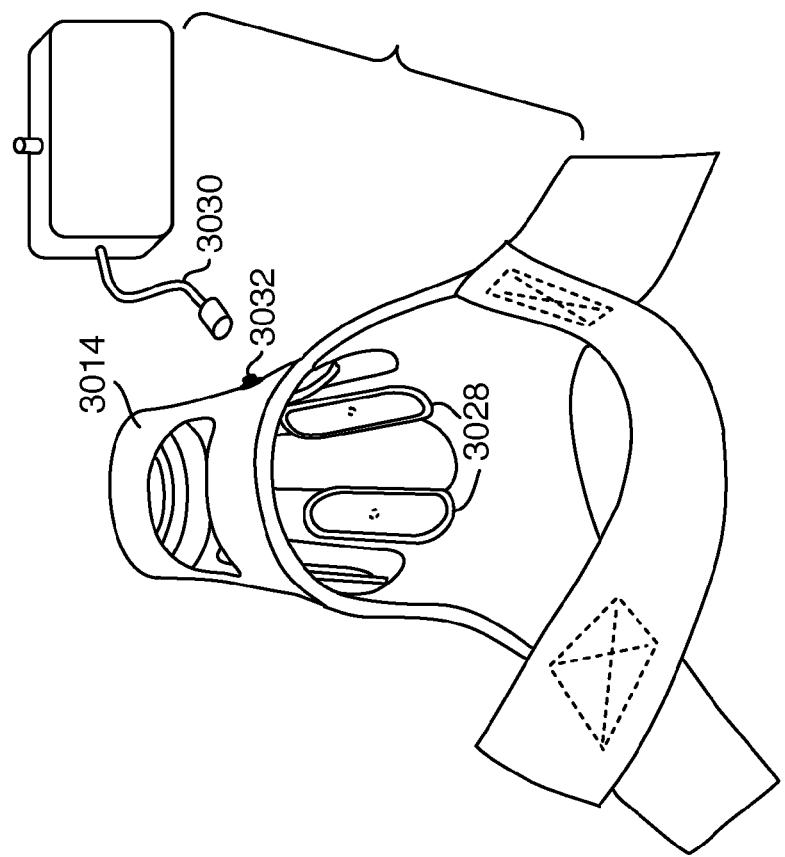
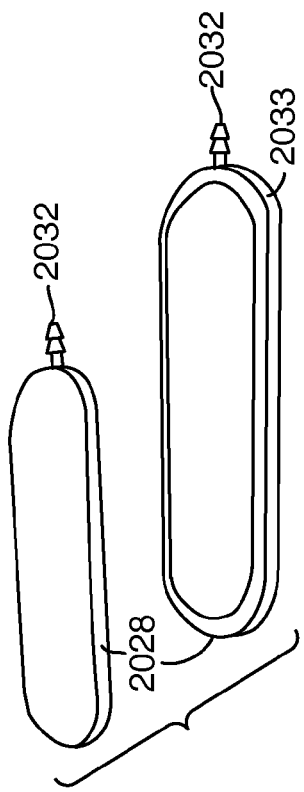
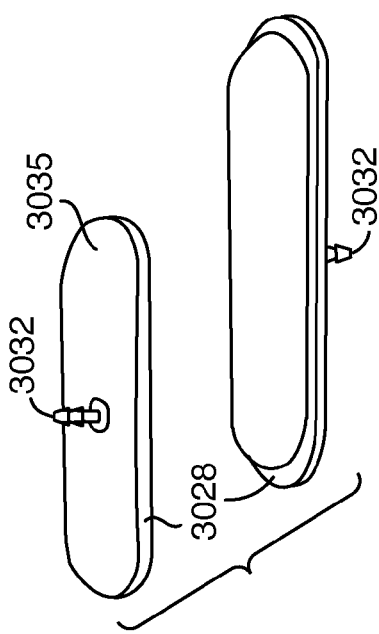
FIG. 10
FIG. 8
FIG. 9

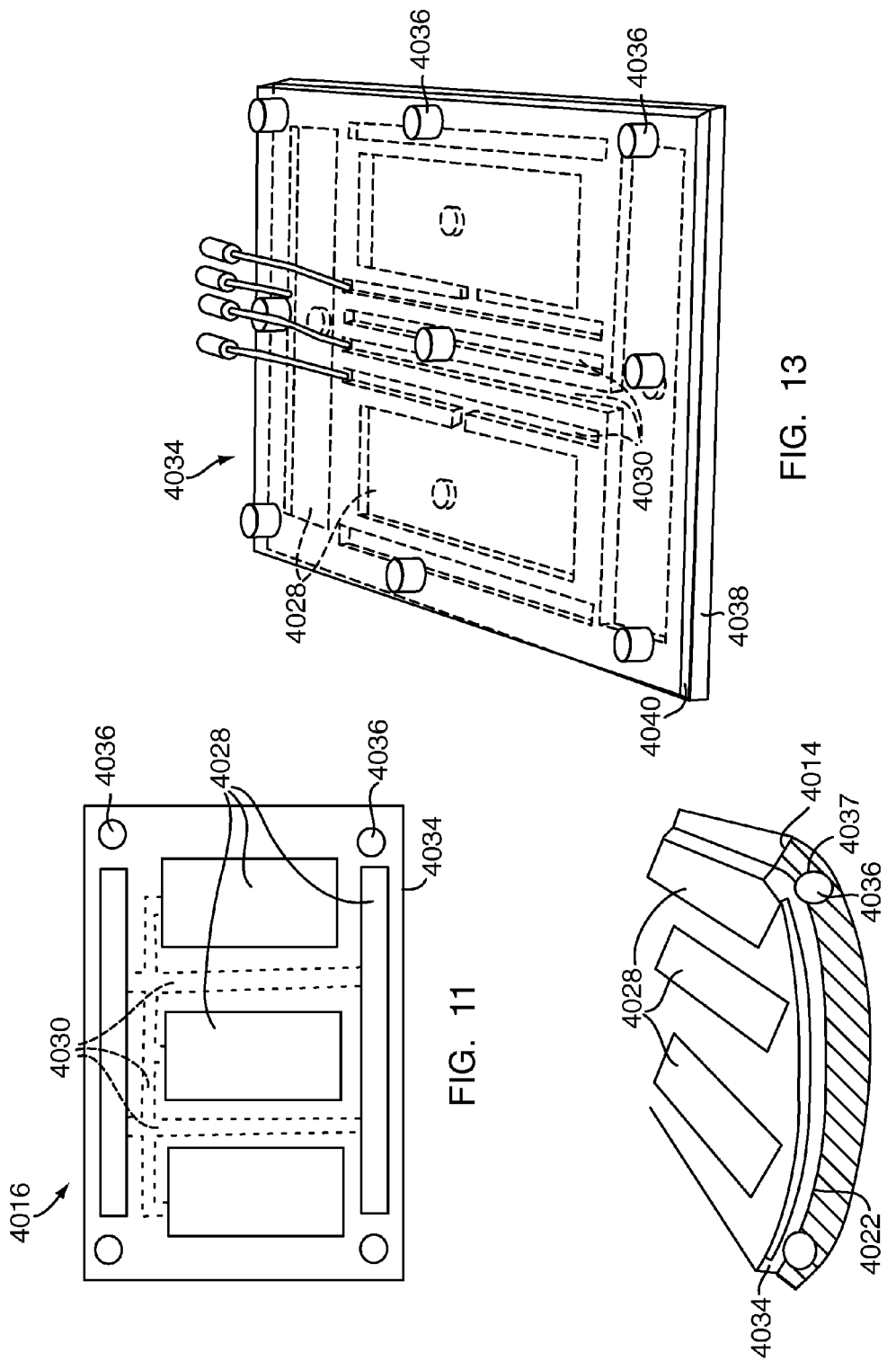

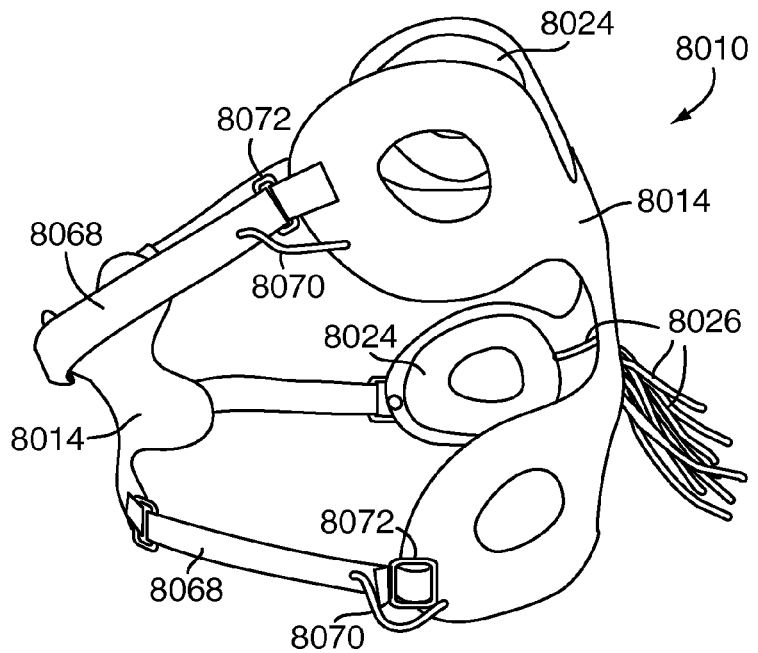
FIG. 28
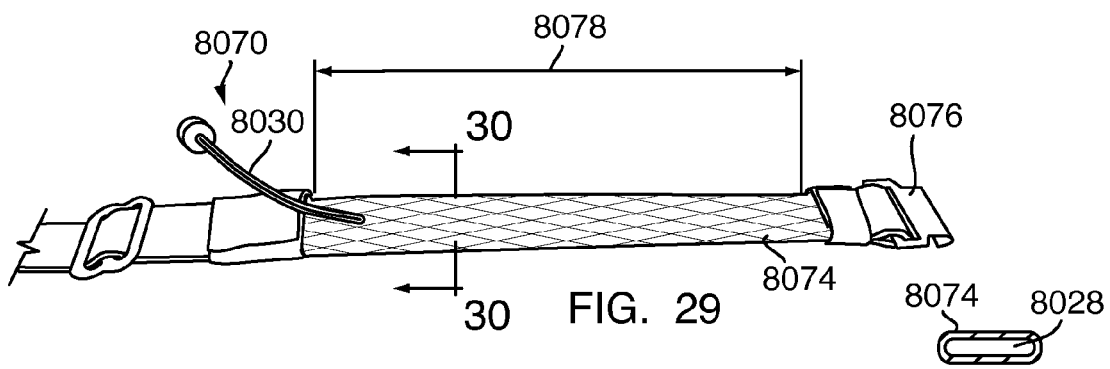
FIG. 29
FIG. 30
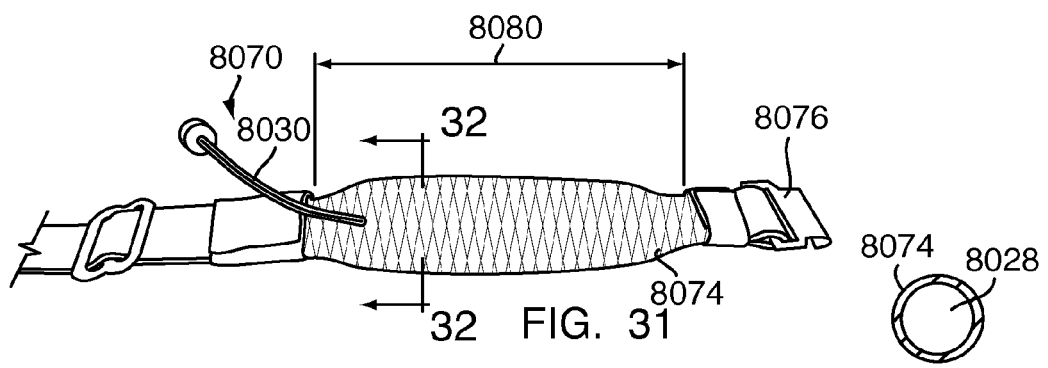
FIG. 31
FIG. 32

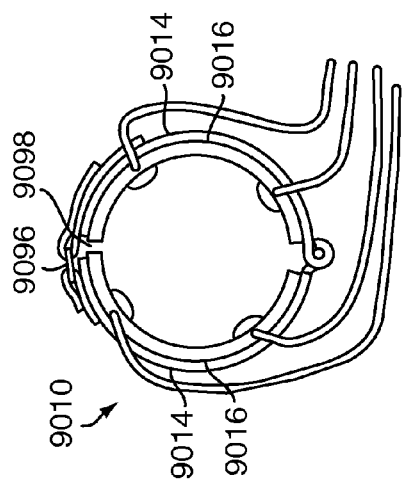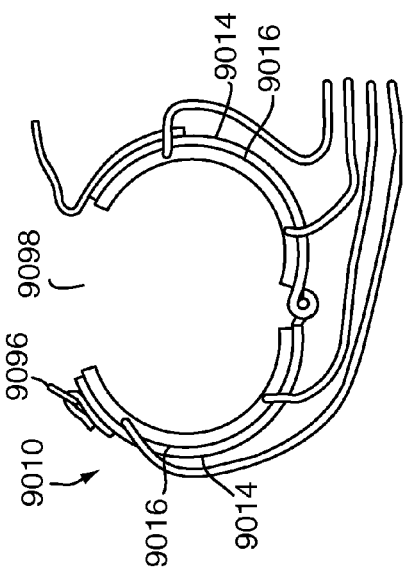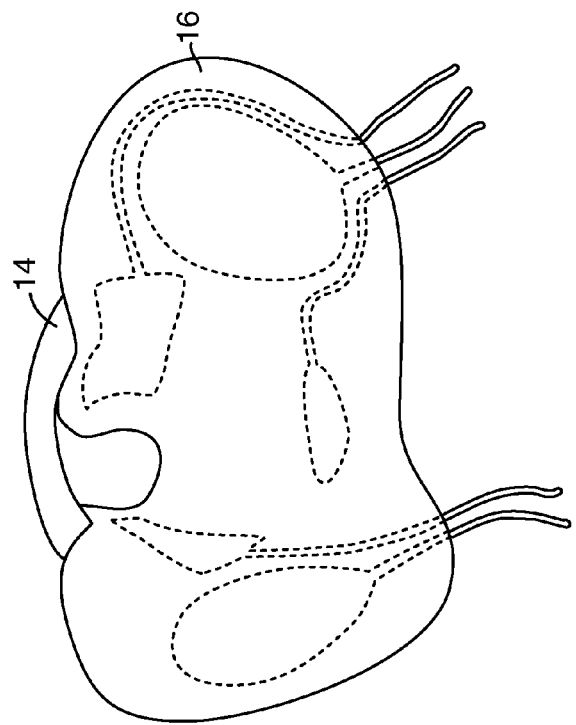

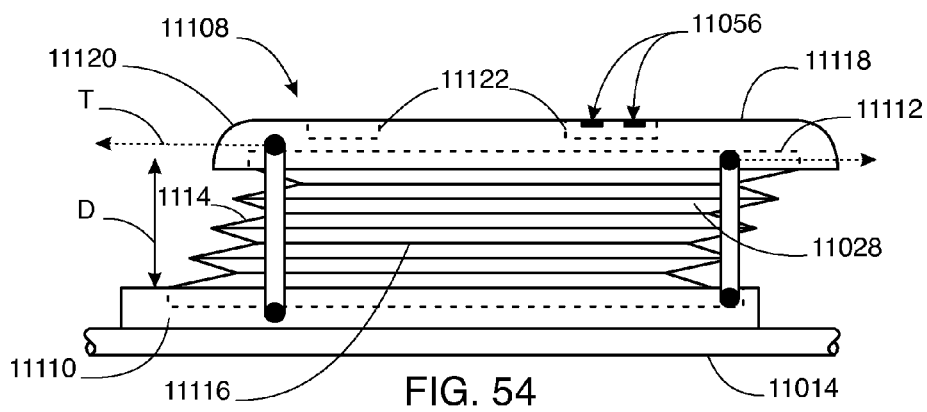
FIG. 54
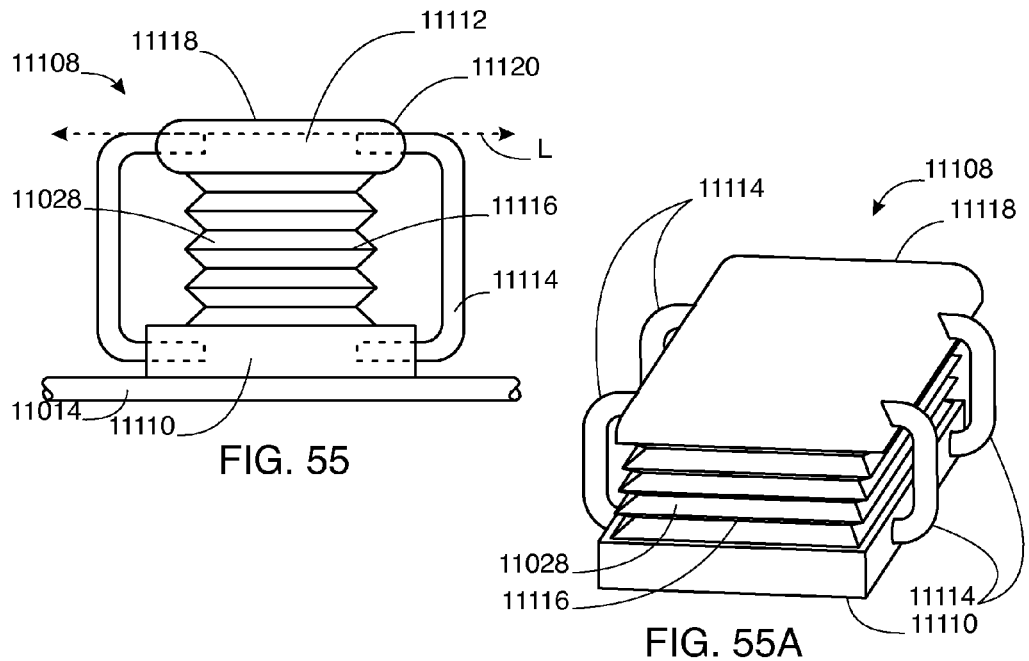
FIG. 55
FIG. 55A
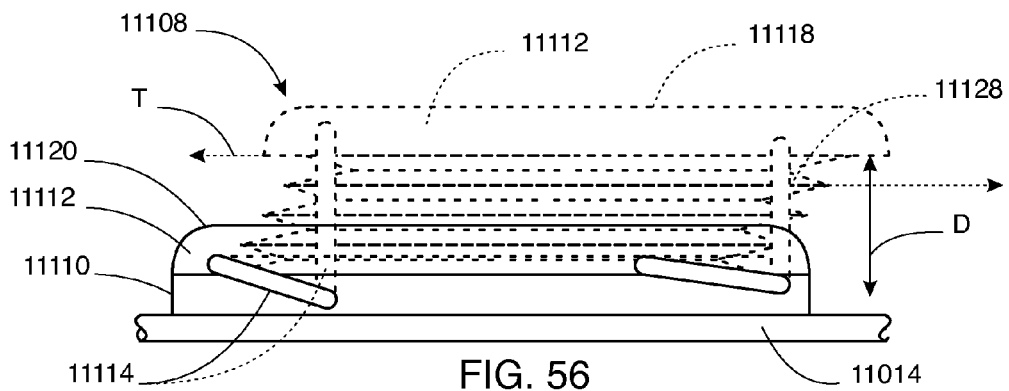
FIG. 56

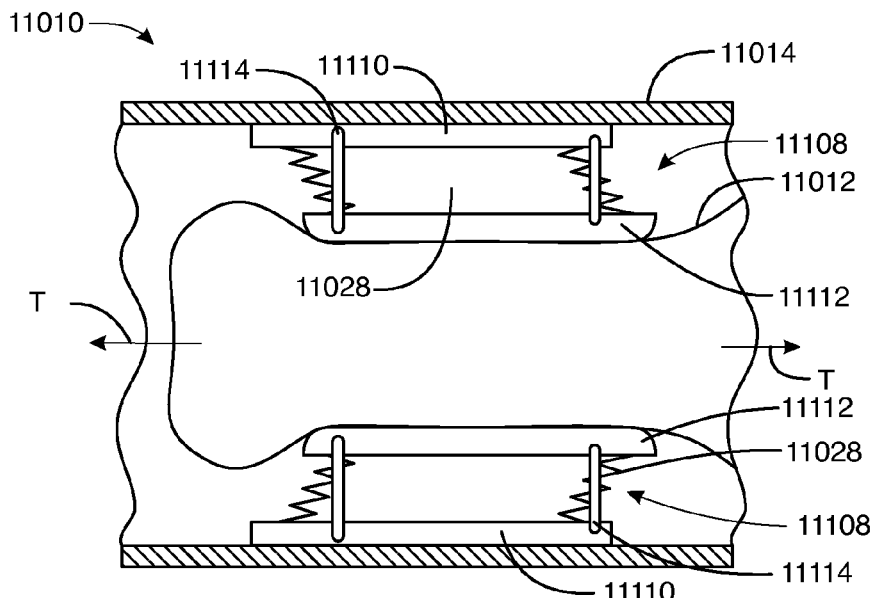
FIG. 59
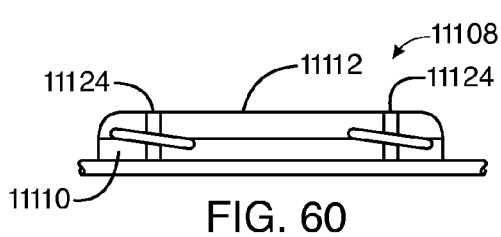
FIG. 60
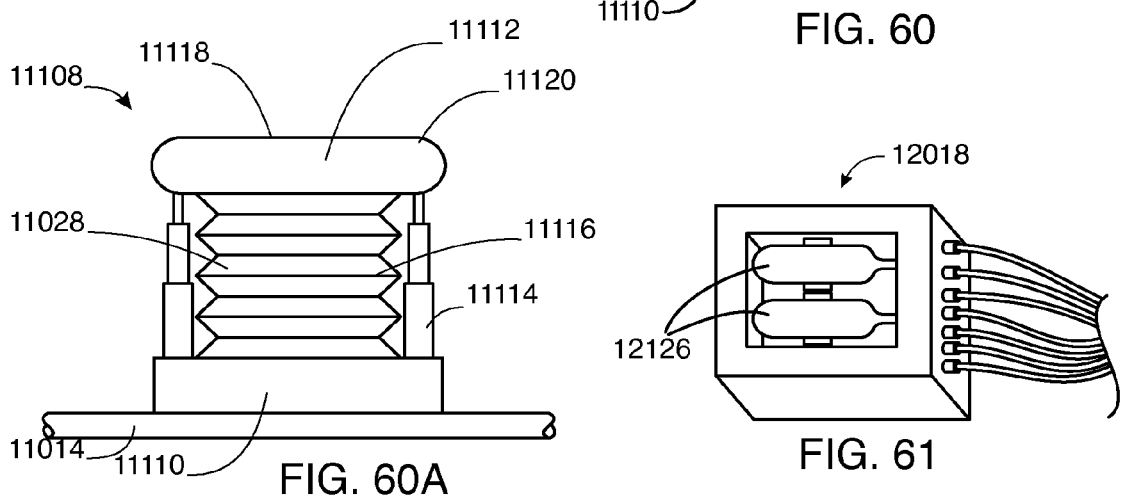
FIG. 60A
FIG. 61
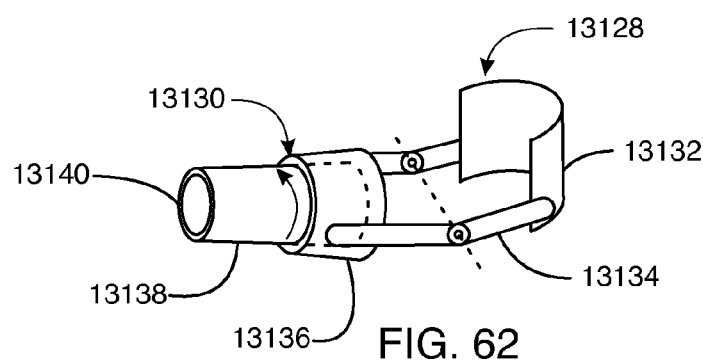
FIG. 62

DYNAMIC SUPPORT APPARATUS AND SYSTEM

CROSS-REFERENCE TO RELATED APPLICATIONS

This application is a continuation of U.S. patent application Ser. No. 12/706,340 filed Feb. 16, 2010, which claims priority to U.S. Provisional Patent Application Ser. No. 61/168,793, filed Apr. 13, 2009, and which is a continuation-in-part of U.S. patent application Ser. No. 12/026,971, filed Feb. 6, 2008, which claims priority from U.S. Provisional Patent Application Ser. No. 60/899,835, filed Feb. 6, 2007, each of which is hereby incorporated by reference in its entirety.

STATEMENT OF GOVERNMENT INTEREST

This invention was made with Government support under Contract Number W911NF-09-C-0035 awarded by the U.S. Army RDECOM ACQ CTR. The Government has certain rights in the invention.

TECHNICAL FIELD

The present invention relates to support apparatuses and more specifically to dynamic support apparatuses.

BACKGROUND INFORMATION

This support apparatus may be used for upper-limb and lower-limb prosthetic devices, or any device with interaction with the body, but for exemplary purposes, the present apparatus will be described in the context of prostheses for upper-limb amputees.

Accordingly, there is a need for a dynamic support apparatus that accommodates users' needs in the interaction with the user. A device that can, in addition to other features, include changing geometry in response to residuum morphing to maintain a secure, comfortable fit with the user's body, and/or maintain a comfortable temperature and moisture environment between the support apparatus and the user's body is desired.

SUMMARY OF THE INVENTION

In accordance with one aspect of the present invention, the dynamic support apparatus includes a frame, a dynamic interface capable of changing its geometry, and a control system. The dynamic interface is disposed on a surface of the frame and has at least one actuator. The control system is operably connected to the dynamic interface by at least one connector.

In accordance with another aspect of the invention, the at least one actuator is a bladder capable of changing geometry when filled with a gas or a liquid. The bladder is capable of changing geometry in a specific direction. In accordance with another aspect of the present invention, the control system is a pneumatic system. A manifold may control the distribution of air to the at least one bladder.

In accordance with another aspect of the present invention, at least one sensor provides information on the stability and fit of the support apparatus to the control system. In accordance with a further aspect of the present invention, the at least one sensor is a pressure transducer. In accordance with another aspect of the present invention, the control system maintains a constant pressure measured by the pressure transducer. In accordance with a further aspect of the present invention, the control system actuates a change in geometry of the dynamic interface based on the information provided by the at least one sensor.

In accordance with another aspect of the present invention, the at least one actuator and the at least one connector are molded inside the dynamic interface. In accordance with a further aspect of the present invention, the at least one actuator and the at least one connector are integrally molded as part of the dynamic interface.

In accordance with another aspect of the present invention, the frame has an opening to allow expansion of the dynamic support apparatus. In a further aspect of the present invention, the dynamic support has a securing mechanism to preclude expansion thereof.

In accordance with another aspect of the present invention, the dynamic support apparatus includes a frame, a dynamic interface capable of changing its geometry, a control system, and a temperature control mechanism. The dynamic interface is disposed on the top surface of the frame and has at least one actuator. The control system is operably connected to the dynamic interface to control the changing geometry of the dynamic interface. The temperature control mechanism is disposed on the top surface of the frame for maintaining a comfortable temperature and moisture environment between the apparatus and the user's body. In accordance with a further aspect of the present invention, the temperature control mechanism has at least one aperture formed within the frame. In accordance with another aspect of the present invention, the temperature control mechanism has at least one duct included in the dynamic interface. In accordance with a further aspect of the present invention, the temperature control mechanism has at least one orifice formed within the dynamic interface. In accordance with a further aspect of the present invention, the temperature control mechanism has at least one temperature sensor.

In another aspect, the present invention relates to a method of fabricating a dynamic interface of a dynamic support apparatus. The method comprises scanning a contour of a residuum to define an outline of an interface between the frame and the residuum. The method also comprises flattening the outline to form a template. The method further comprises machining the template into a mold. The method additionally comprises pouring a material for the dynamic interface to half a desired final thickness of the dynamic interface to create a first interface layer. The method also comprises placing actuators and connectors on the first interface layer. The method further comprises pouring the material for the dynamic interface to the desired final thickness of the dynamic interface to create a second interface layer. The method additionally comprises removing the resulting dynamic interface from the mold.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

These and other features and advantages of the present invention will be better understood by reading the following detailed description, taken together with the drawings wherein:

FIG. 8 is a perspective view showing the top and bottom of one embodiment of an actuator of the dynamic support apparatus;

FIG. 9 is a perspective view showing the top and bottom of another embodiment of an actuator of the dynamic support apparatus;

FIG. 10 is a perspective view of a dynamic support apparatus with the actuators of FIG. 9 installed;

FIG. 11 is a top view of one embodiment of the dynamic interface of a dynamic support apparatus;

FIG. 12 is a side view of the dynamic interface of FIG. 11 with respect to the frame of an embodiment of a dynamic interface;

FIG. 13 is a bottom view of one embodiment of the dynamic interface of a dynamic support apparatus;

FIG. 28 is a structural view of the dynamic support apparatus of FIGS. 26 and 27;

FIG. 29 is a perspective view of one embodiment of an un-actuated active strap of a dynamic support apparatus;

FIG. 30 is a cross-sectional view of the active strap of FIG. 29;

FIG. 31 is a perspective view of the active strap of FIGS. 29 and 30 when actuated;

FIG. 32 is a cross sectional view of the actuated active strap of FIG. 31;

FIG. 43 is a front assembled view of the dynamic interface of FIG. 42;

FIG. 45 is a rear perspective view of the dynamic support apparatus of

FIG. 43 as worn by a patient;

FIG. 46 is a top view of an alternative embodiment of a dynamic support apparatus;

FIG. 47 is the dynamic support apparatus of FIG. 46 when partially opened;

FIG. 54 is a side view of a laterally stabilized bladder in an actuated state according to an embodiment of the present invention;

FIG. 55 is a front view of the laterally stabilized bladder of FIG. 54;

FIG. 55A is a front perspective view of the laterally stabilized bladder of FIG. 55;

FIG. 56 is a side view of the laterally stabilized bladder of FIG. 54 in an inactuated state;

FIG. 59 is a cross-sectional view of the prosthetic support apparatus of FIG. 58 in an actuated state;

FIG. 60 is a side view of the laterally stabilized bladder of FIG. 56 with a resilient member;

FIG. 60A is a front view of another embodiment of a laterally stabilized bladder;

FIG. 61 is a perspective view of a control system according to another embodiment of the present invention;

FIG. 62 is a perspective view of a prosthetic support apparatus according to yet another embodiment of the present invention.

DETAILED DESCRIPTION OF THE PREFERRED EMBODIMENTS

Figure 1:
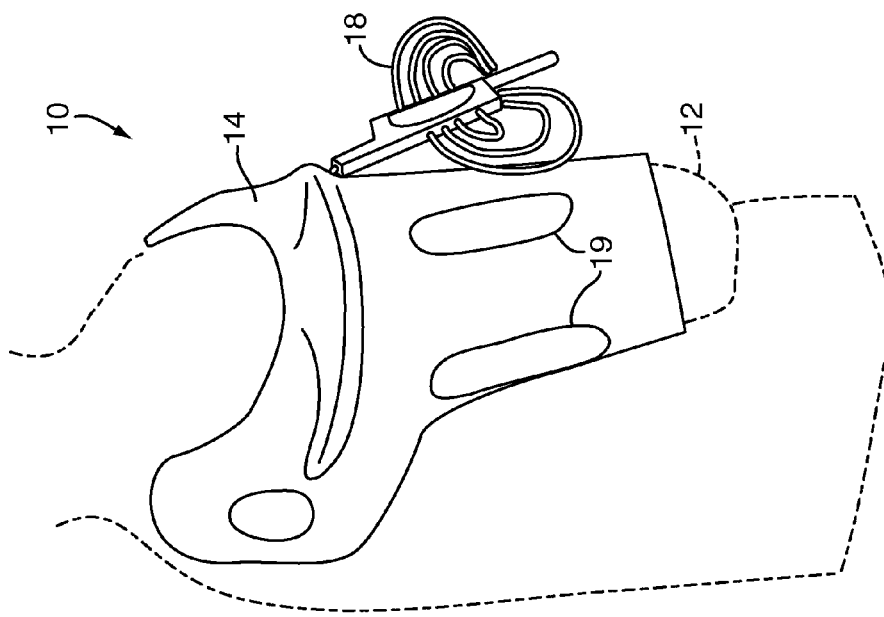
FIG. 1 is a perspective view of one embodiment of a dynamic support apparatus.

For exemplary purposes, the support apparatus will be described in the embodiment of a support apparatus 10 for an upper-limb trans-humeral (TH) prosthesis, as seen in FIG. 1, such as the various prosthetic arms described in U.S. patent application Ser. No. 12/027,141, filed Feb. 6, 2008, and the U.S. patent application entitled ARM PROSTHETIC DEVICE, filed on the same day as the present application and assigned to the same assignee, each of which is hereby incorporated by reference in its entirety.

Figure 2:
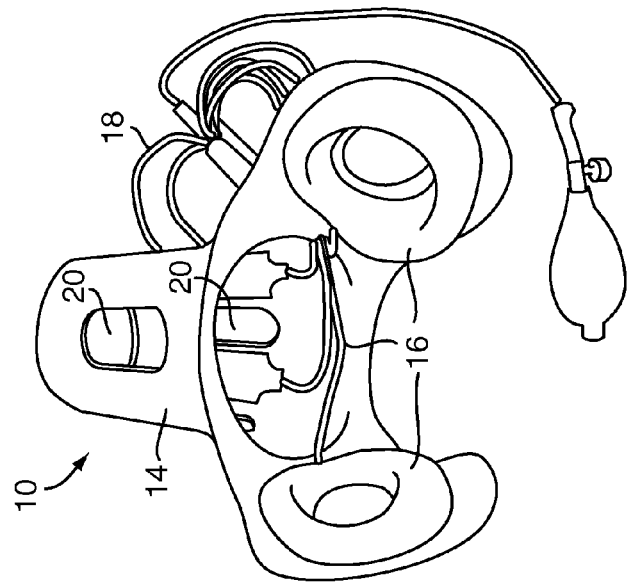
FIG. 2 is a top view of the embodiment of the dynamic support apparatus of FIG. 1.
Figure 63:
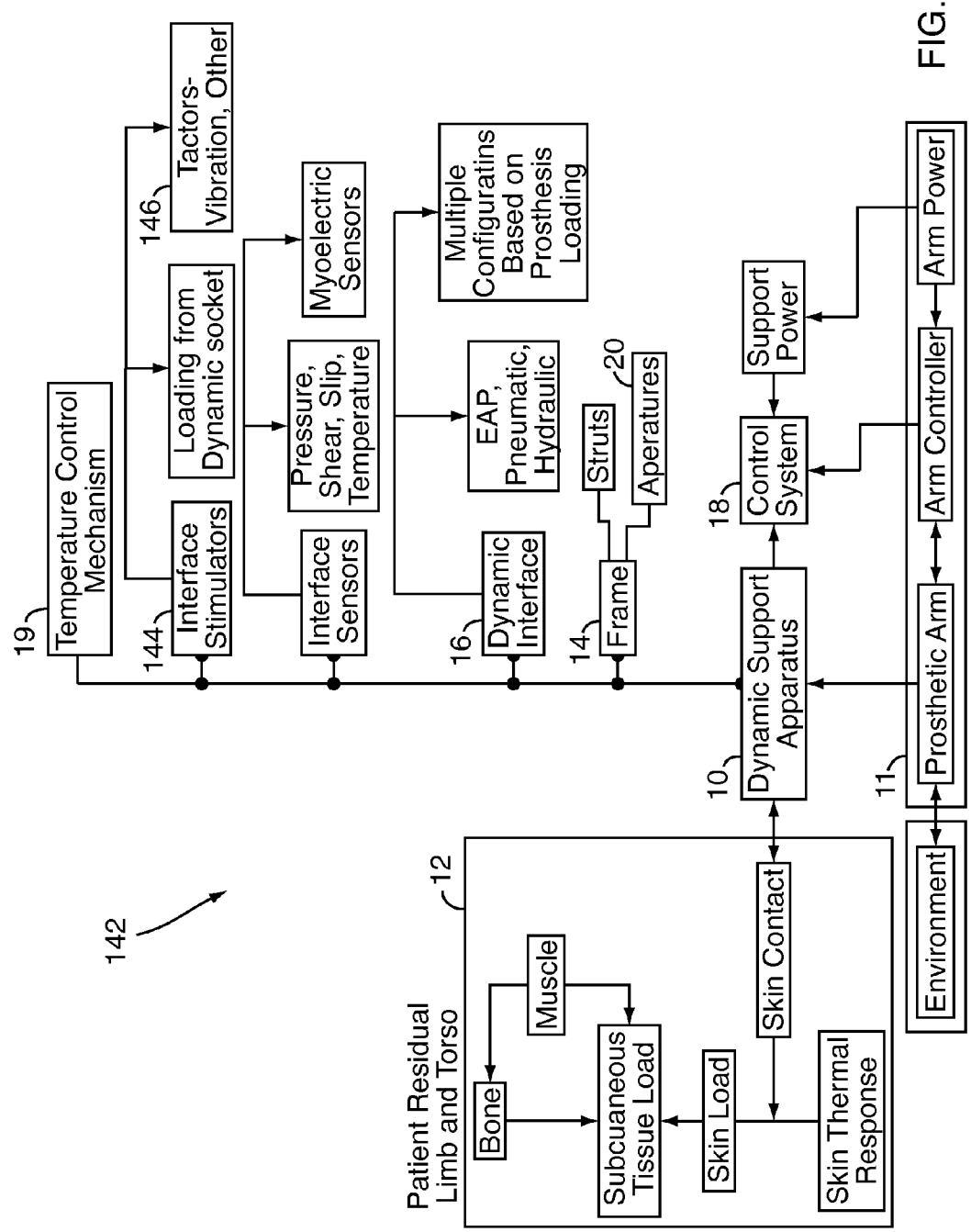
FIG. 63 is a schematic diagram of a dynamic support system according to an embodiment of the present invention.

Referring to FIG. 2, the support apparatus 10, which is utilized to removably adhere a prosthesis 11, shown in FIG. 63, to an upper-limb residuum 12 (FIG. 1), includes a frame 14, a dynamic interface 16, a control system 18, and a temperature control mechanism 19. The frame may be made of high tech composite material such as carbon fiber.

In one embodiment, the frame 14 may be open and have a plurality of apertures 20. The structural members of the frame of this embodiment may be strategically placed to maximize the openness of the apparatus. Additionally, the plurality of apertures 20 may be the temperature control mechanism or function as a part of the temperature control mechanism.

The dynamic interface 16 is disposed on a top surface 22 of the frame closest to the upper-limb residuum 12. The dynamic interface 16 includes one or more actuators 24 of various shapes and sizes that can be positioned either longitudinally and/or circumferentially along the frame 14. The actuators 24 are capable of changing their geometry and volume to secure the support apparatus 10 to the residuum 12, shown in FIG. 1, and to account for morphing in the residuum 12.

As discussed above, the support apparatus 10 includes apertures 20 to address both structural and temperature concerns. In addition, the apertures 20 may be designed to provide relief to the residuum 12, shown in FIG. 1, when the support apparatus 10 is secured thereonto. For instance, the apertures 20 may provide space to allow the soft tissue of the residuum 12, shown in FIG. 1, to move away from the actuators 24, thereby minimizing the amount of soft tissue between the load bearing surfaces of the support apparatus 10, i.e. the actuators 24, and the bone within the residuum 12, shown in FIG. 1. Thus, the apertures 20 allow the soft tissue of the residuum 12 to escape the areas of contact with the actuators 24, thereby providing relief to the user and allowing the actuators 24 to engage to bone within the residuum 12, shown in FIG. 1.

Although described as apertures 20, in some embodiments, the support apparatus 10 may additionally include at least one hollow cavity to provide another means for soft tissue escape. Thus, as the actuators 24 change their geometry to secure the support apparatus 10 to the residuum 12, shown in FIG. 1, the soft tissue may be displaced into the hollow cavities during actuation to provide relief to the user.

Figure 3:
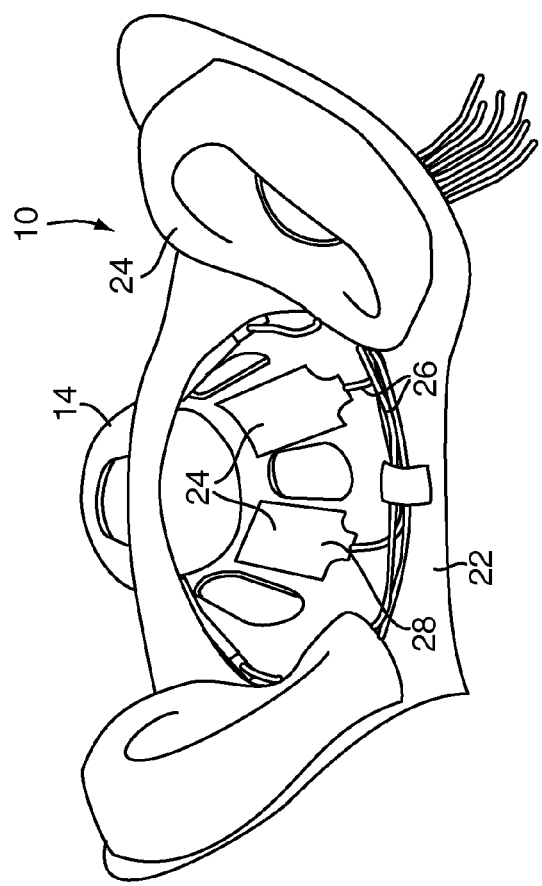
FIG. 3 is an internal view of the embodiment of the dynamic support apparatus of FIGS. 1 and 2.

Referring to FIG. 3, the actuators 24 may be bladders 28 filled with air, incompressible gas or incompressible liquid, electroactive polymers (EAPs), or other types of actuators capable of changing their geometry. The dynamic interface also includes one or more connectors 26 that connect the actuator(s) 24 to the control system 18. The connector(s) may be fluid paths, tubes, wires, or other similar channels.

Figure 4:
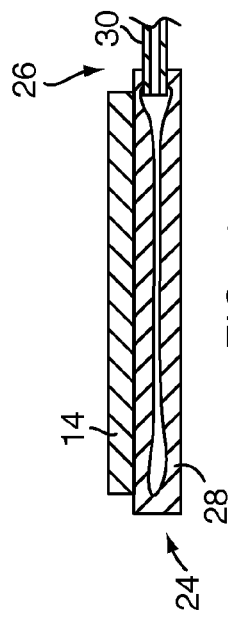
FIG. 4 is a cross-sectional view of one embodiment of an actuator of the dynamic support apparatus in an inactuated state.
Figure 5:
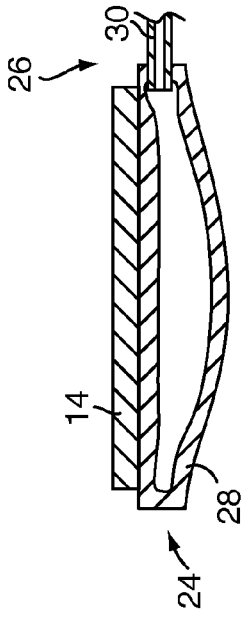
FIG. 5 is a cross-sectional view of the actuator of FIG. 4 of the dynamic support apparatus in an actuated state.
Figure 6:
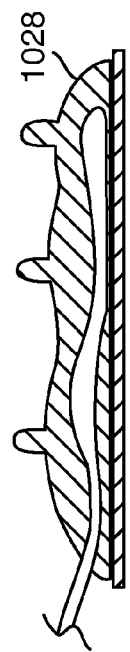
FIG. 6 is a cross-sectional view of another embodiment of an actuator of the dynamic support apparatus in an inactuated state.
Figure 7:
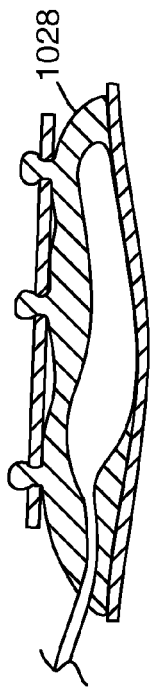
FIG. 7 is a cross-sectional view of the actuator of FIG. 6 of the dynamic support apparatus in an actuated state.

Referring to FIGS. 4 and 5, in an embodiment having bladders 28 for actuators 24 and fluid path connectors 30 for connectors 26, the bladder 28 will change geometry from an inactuated position shown in FIG. 4 to the actuated position shown in FIG. 5 when filled with air. Although the bladder 28 is shown with a substantially uniform cross section in FIGS. 4 and 5, the same functionality may be obtained from the bladder 1028 having a non-uniform cross-section shown inactuated in FIG. 6 and actuated in FIG. 7, wherein the like numerals represent the like elements.

Referring to FIG. 8, in a further embodiment, the bladders 2028 may have bladder inlets 2032 to facilitate the connection of the fluid path connectors 30, shown in FIGS. 4 and 5. The bladder inlets 2032 may be located at any position on a periphery 2033 of each bladder 2028 to accommodate the desired fluid path connector routing configuration. Referring to FIG. 9, an alternative embodiment positions the bladder inlet 3032 on a body 3035 of the bladder 3028. In this embodiment, as seen in FIG. 10, the bladder inlet 3032 may pass through the frame 3014 to facilitate connection to the fluid path connectors 3030.

In one embodiment, the frame has an outer shell and an inner shell. Here, the dynamic interface may be disposed between the outer shell and the inner shell. The inner shell may also have apertures to dictate the shape the actuator(s). For example, if the actuator(s) are bladders, the inner shell apertures would dictate the shape of the bladder as it is inflated.

In another alternative embodiment, referring to FIGS. 11 and 12, the dynamic interface 4016 is a single integrated layer 4034 disposed on the top surface 4022 of the frame 4014. For example, in an embodiment having bladders 4028 with fluid path connectors 4030, the bladders 4028 and fluid paths connectors 4030 are embedded into a single layer of material that is placed on top of the frame 4014. The single integrated layer 4034 may be made of any material that allows for morphable chambers that can house or act as actuators of variable geometry. Such material may be silicon or rapid prototype molding material covered with a layer of silicon. The single integrated layer 4034 may also have nodules 4036 to attach to the frame 4014 having corresponding apertures 4037 for the nodules 4036. In some embodiments, the nodules 4036 are protrusions. The nodules 4036 do not have to be round bumps as depicted in one embodiment of the apparatus.

Figure 14:
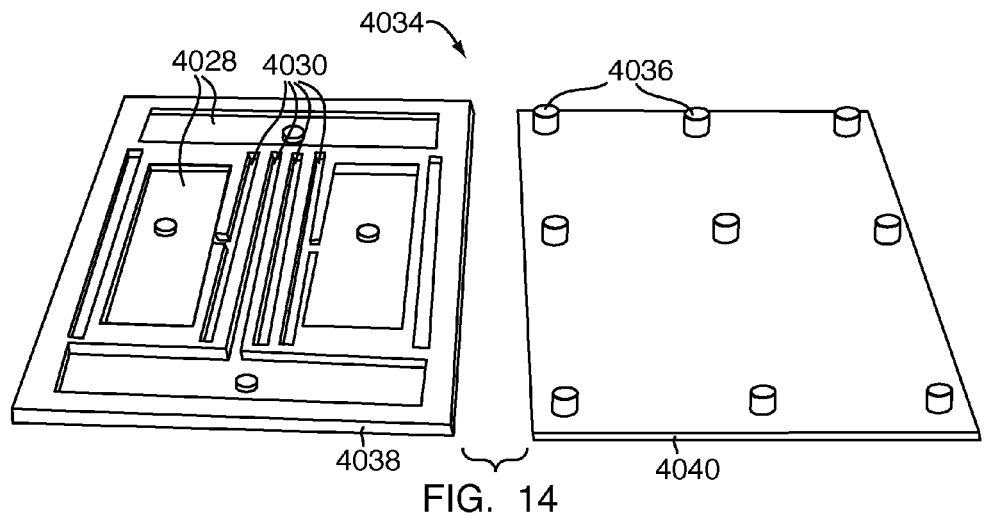
FIG. 14 is an exploded view of the dynamic interface of FIG. 13.

Referring to FIG. 13, the bladders 4028 and fluid path connectors 4030 may be molded as a part of the single integrated layer 4034, such that the layer itself contains internal paths and compartments that serve as the fluid path connectors 4030 and bladders 4028, respectively. The molded single integrated layer 4034 may also have nodules 4036 to attach to a frame having corresponding apertures 4037. As seen in FIG. 14, the single integrated layer 4034 may be constructed by molding an actuation layer 4038, containing the necessary bladders 4028 and fluid path connectors 4030, and a connection layer 4040, containing nodules 4036 for attaching the single integrated layer 4034 to the frame. The actuation layer 4038 and the connection layer 4040 can then be bonded together to form the single integrated layer 4034, as seen in FIG. 13. The molded single integrated layer 4034 may be fabricated from any material that allows morphable chambers that can act as actuators of variable geometry. Such material may be silicon or rapid prototype molding material covered in a layer of silicon. Additionally, bladders, such as the bladders 2028, shown in FIG. 8, or the bladders 3028, shown in FIG. 9, with their unique characteristics, may also be embedded in the molded single integration layer 4034, which may provide the dynamic interface 4016 with characteristics of both the bladders and the molded single integration layer 4034, for example, to increase actuation while increasing stability.

The dynamic interface 16 allows the support apparatus 10 to morph and adapt to the function of the residuum 12. For example, in an embodiment having actuators 24 that are bladders 28 filled with incompressible gas, when the residuum 12 morphs, possibly due to tissue volume variation or loading, the bladders 28 either inflate or deflate to adjust to the residuum 12 morphing and to maintain a secure and comfortable fit on the residuum 12.

The control system 18 controls the changing geometry of the actuators 24. The control system 18 may be hydraulic, pneumatic, electromechanical, mechanical, or any other actuator type mechanism that allows the actuators 24 to change geometry. In our exemplary embodiment, the bladders 28 are controlled by a pneumatic system and connected to the system by the fluid paths connectors 30.

Figure 15:
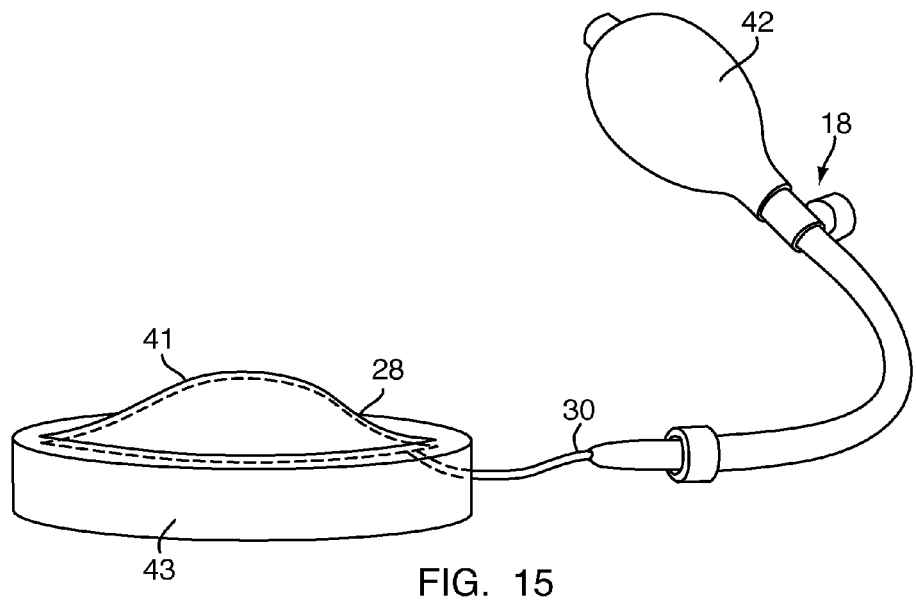
FIG. 15 is a perspective view of one embodiment of an actuator and control system of a dynamic support apparatus.

Referring now to FIG. 15, one embodiment of the control system 18 is shown as a manual system with a pressure bulb 42 that is connected to the bladder 28 by one or more fluid path connectors 30. When the user begins to feel instability or discomfort with the fit of the support apparatus 10, the user squeezes the pressure bulb 42, which can be set to either increase or decrease the air or liquid pressure in the bladder 28, thus adjusting the fit of the support apparatus 10 to the user's liking. If more than one bladder 28 is used, the user may be able to adjust the pressure in each individual bladder 28.

Still referring to FIG. 15, in this embodiment, the bladder 28 is laser welded. By laser welding a thin sheet 41 of bladder material to a substantially thicker sheet 43 of bladder material or a stable base material, such as an injection molded flexible plastic, the actuation can be isolated to a desired direction. As seen in FIG. 15, the bladder 28 deforms in the direction of the thin sheet 41 of material, while the remainder of the bladder 28 remains substantially unchanged.

Figure 16:
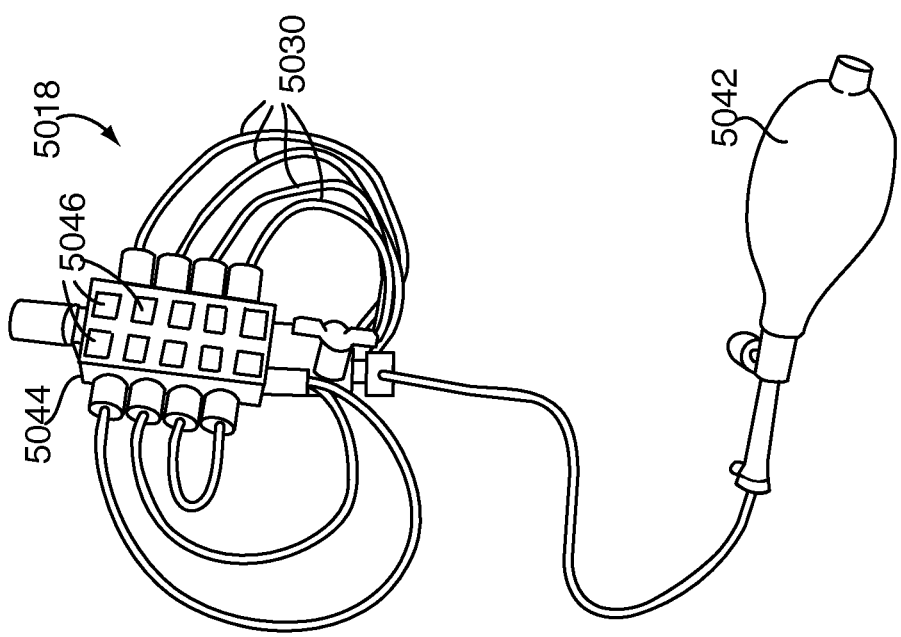
FIG. 16 is one embodiment of a manual control system of a dynamic support apparatus.

Referring now to FIG. 16, in an alternative embodiment of the control system 5018, the pressure bulb 5042 is connected to a plurality of bladders by one or more fluid path connectors 5030 through a manifold 5044. The manifold may have pressure selectors 5046 allowing the user to adjust the pressure in the plurality of bladders by different amounts with the pressure bulb 5042. The user may thus preset the pressure selectors 5046 to provide optimal adjustment of the support apparatus. Additionally, the pressure selectors 5046 also allow the user to target one or more specific bladder(s) of the plurality of bladders, such that pressure can be adjusted solely in the targeted bladders) while pressure in the rest of the plurality of bladders remains unchanged. This targeting capability permits pinpoint adjustment based on localized instability or discomfort.

Figure 17:
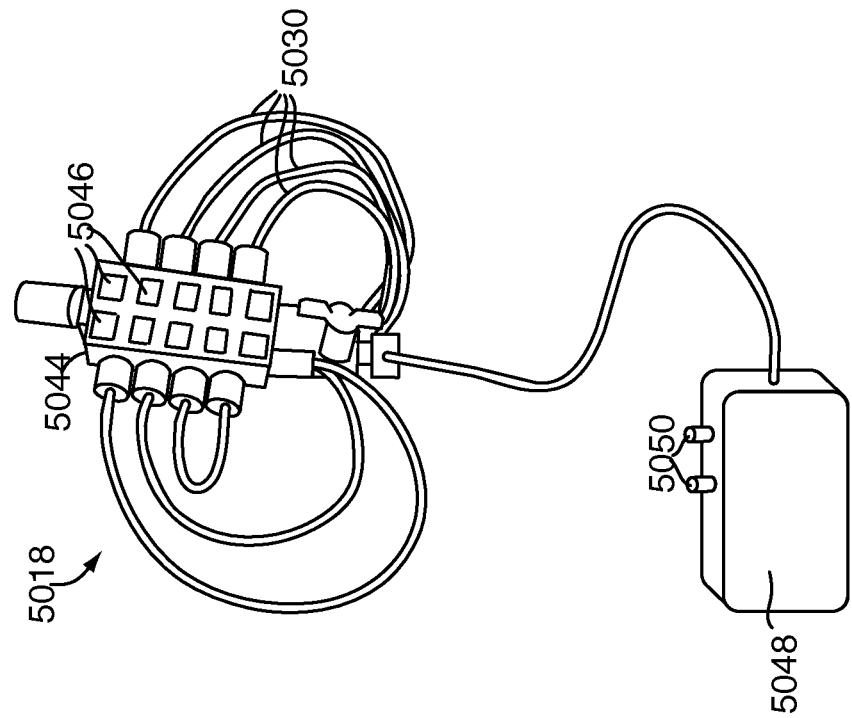
FIG. 17 is one embodiment of a manual control system of a dynamic support apparatus.

Referring now to FIG. 17, the control system 5018 includes an electric pump 5048 in place of the pressure bulb 5042 for adjusting the pressure in the plurality of bladders. Pump control 5050 allows the user to either increase or decrease the pressure in the bladders.

Figure 18:
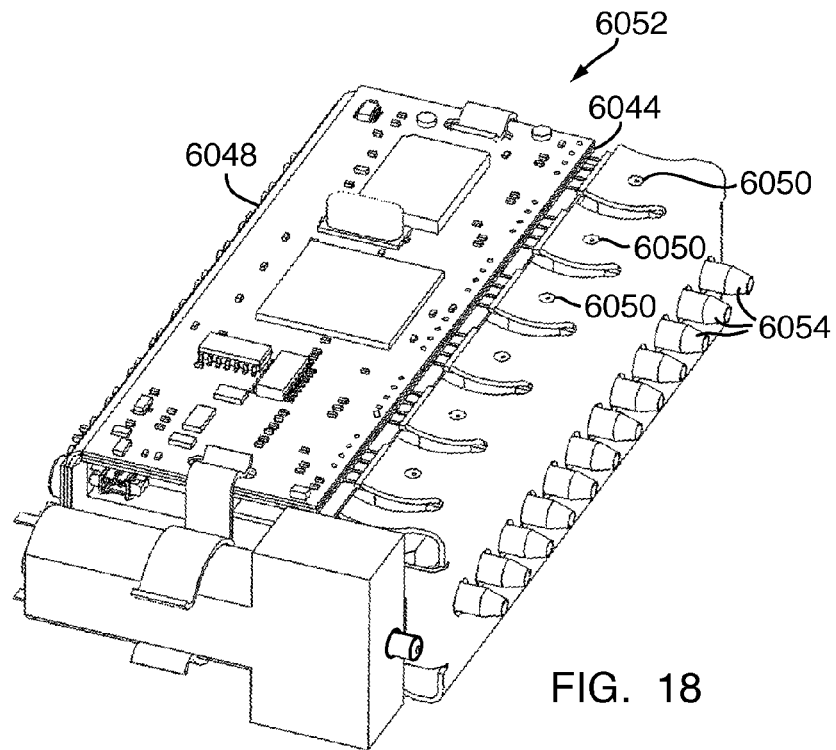
FIG. 18 is an internal perspective view of one embodiment of a control unit of a dynamic support apparatus.
Figure 19:
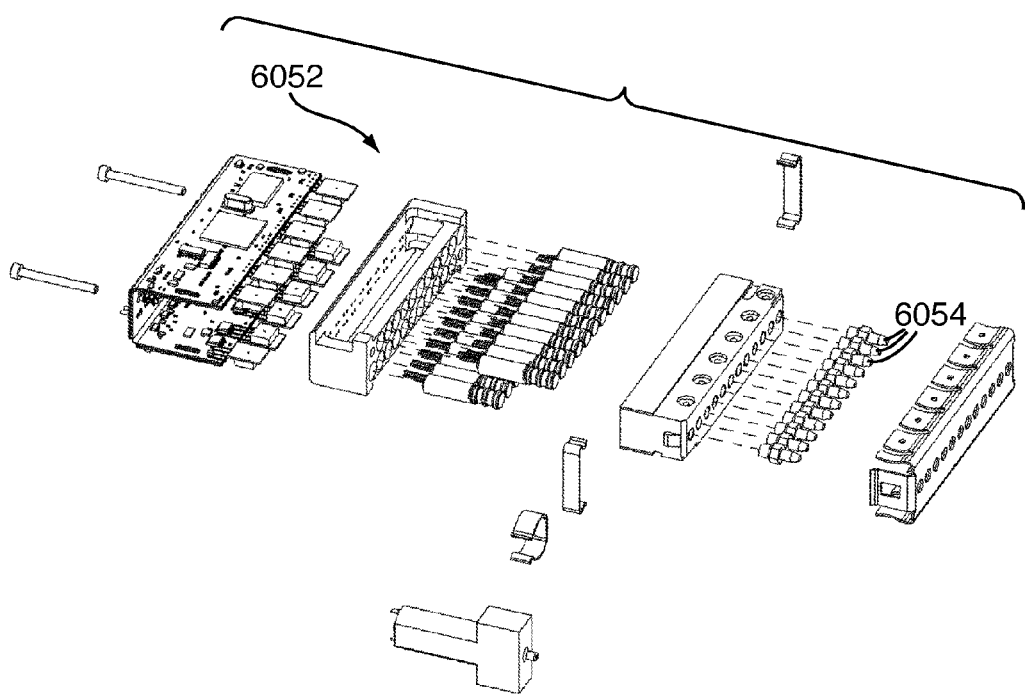
FIG. 19 is an exploded view of the control unit of FIG. 18.

Referring to FIGS. 18 and 19, an alternate embodiment incorporates the electric pump 6048, the pump control 6050, and the manifold 6044 into a control unit 6052. The fluid path connectors are attached to manifold outlets 6054, allowing adjustment of each bladder using the pump control 6050. The manifold 6044, may be located in an accessible location, such as attached to the user's belt, or attached to the support apparatus itself.

Figure 20:
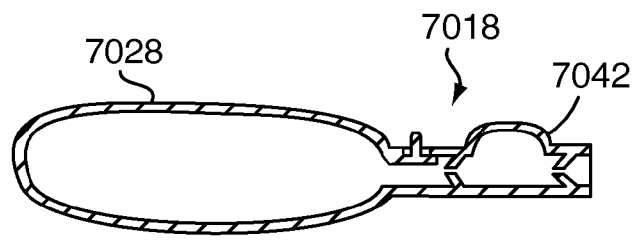
FIG. 20 is a cross-sectional view of one embodiment of an actuator and control system.
Figure 21:
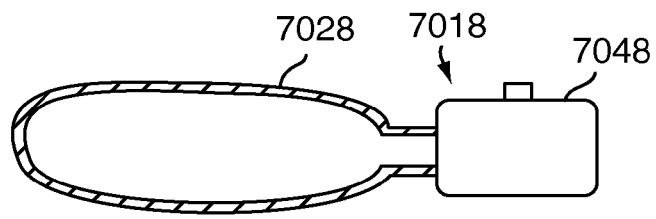
FIG. 21 is a cross-sectional view of one embodiment of an actuator and control system.

Referring now to FIGS. 20 and 21, an alternate embodiment integrates each bladder 7028 and its control system 7018. In the embodiment shown in FIG. 20, the control system 7018 is a pressure bulb 7042. In the embodiment shown in FIG. 21, the control system 7018 is an electric pump 7048. In such an embodiment, the patient would adjust the pressure of each bladder 7028 by actuating its integrated control system 7018.

The control system 18 may be an active control system that provides real-time adjustments in each actuator 24 to accommodate prosthetic load and user posture and to anticipate user needs. Referring back to FIGS. 18 and 19, with the exemplary embodiment having bladders 28 as actuators 24, the control unit 6052 may include an active control system for activating the inflation/deflation of the bladders. The active control system may be in place of, or in addition to, the manual pump control 6050. The active control system may have an input mechanism for gathering readings on the stability and fit of the support apparatus 10 with the residuum 12.

Figure 22:
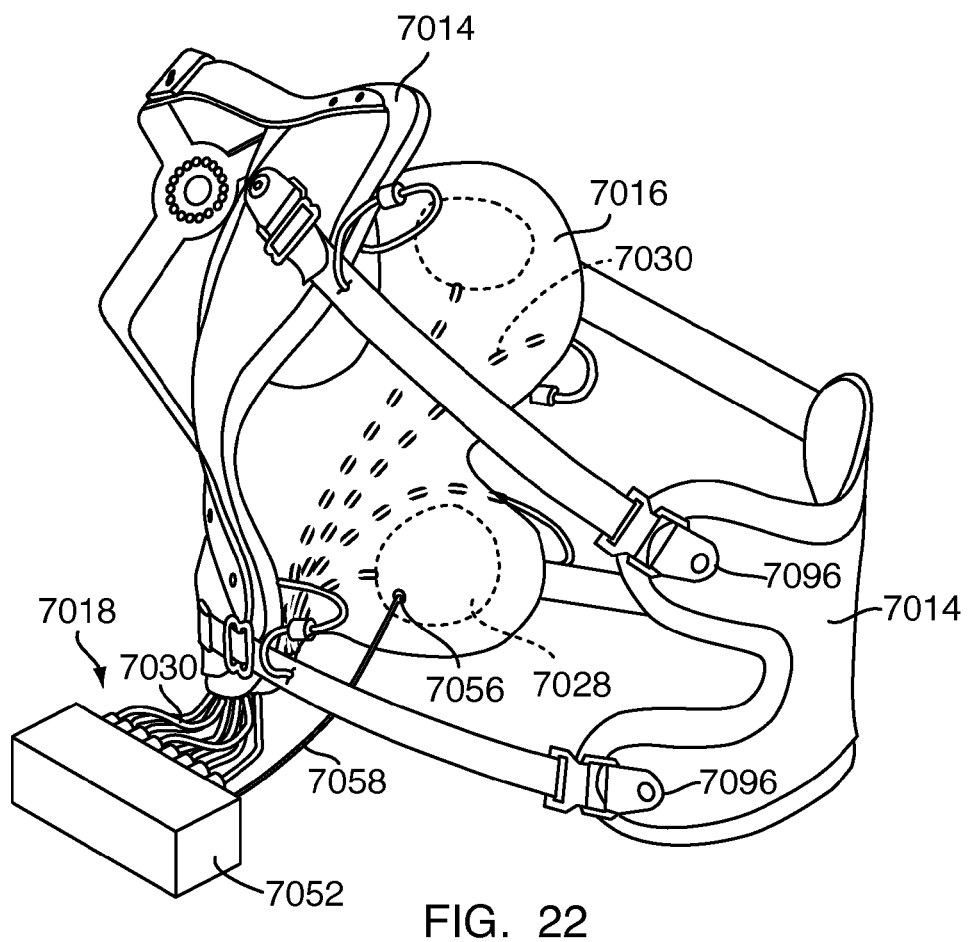
FIG. 22 is a perspective view of one embodiment of a dynamic support apparatus.

In some embodiments, the input mechanism includes sensors, such as pressure transducers, and feedback loops. The sensors may be placed on the inner shell of the frame, on the actuator(s), on the connector(s) connected to the actuator(s), or in any other suitable location, for providing information on the stability and fit of the support apparatus, as should be obvious to those skilled in the art. Controlled by a computer, the sensor(s) determine the pressure in the actuator(s) and, with the feedback loops, signals are sent to the control unit to either increase or decrease the actuator's pressure, possibly by inflation or deflation, thereby changing the volume of the actuator to exert the needed force to maintain the support apparatus's secure fit with the user's body. The computer for controlling the sensors is preferably integrated into the control unit of the control system 18. Referring to FIG. 22, with the exemplary embodiment having bladders 7028 as actuators 7024, a pressure sensor 7056 may be placed on the bladder 7028 to provide fit information to the control unit 7052 through a sensor connector 7058. In this embodiment, if a loose fit is detected by pressure sensor 7056, i.e. the sensed pressure is low, a signal is sent to the control unit 7052 to increase the pressure in the corresponding bladder 7028 until a high pressure is sensed and therefore a stable condition is achieved. In this embodiment, the active control system adjusts the pressure of each actuator 7024 in response to the part of the morphing residuum in contact with that actuator. This embodiment does not necessarily maintain a constant pressure in each bladder 7028 nor does it necessarily maintain a total constant pressure against the residuum.

An alternative embodiment includes an active control system with sensors 7056 and feedback loops that maintain constant pressure in each actuator 7024. For example, in an embodiment having bladders 7028, the sensors 7056 and feedback loops may be placed on each bladder 7028 or on each fluid path 7030 of each bladder 7028. The sensors 7056 may be programmed to take an initial pressure reading of a bladder 7028. The sensors 7056 then take continuous pressure readings of the bladder 7028, comparing these readings to the initial pressure. As the bladder pressure changes, the sensors 7056 and feedback loops send signals to the control unit 7052, which adjusts the pressure in the bladder 7028 to maintain the initial bladder pressure. Maintaining a constant pressure in the bladders 7028 can correspond to maintaining a constant fit between the support apparatus and the residuum.

Figure 23:
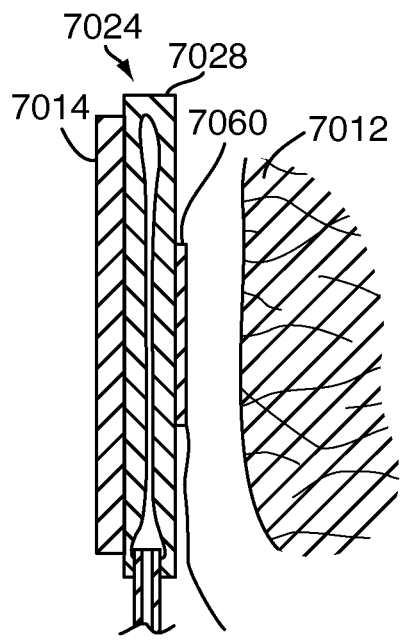
FIG. 23 is a cross-sectional view of an un-actuated actuator and sensor unit.
Figure 24:
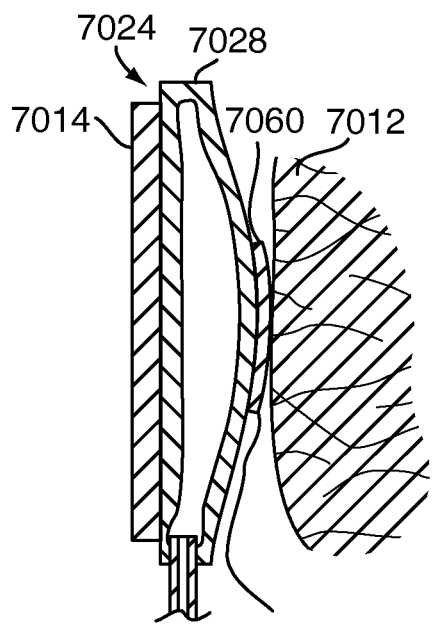
FIG. 24 is the cross-sectional view of FIG. 23 with the actuator actuated.

Referring to FIGS. 23 and 24, the active control system may also include EMG electrodes 7060 for providing control input to the control unit 7052. The EMG electrodes 7060 may be placed between the actuator(s) 7024 and the skin of the residuum 7012, on a separate layer or on each actuator 7024. The EMG electrodes 7060 sense voluntary underlying muscle activity and can be used to control some function of the prosthesis. In a support apparatus having bladders 7028, the bladders 7028 control the downward pressure of the EMG electrodes 7060 on the skin of the residuum 7012. This control of the downward force eliminates unintentional relative movement of the EMG electrodes 7060, which generates an artifact signal, a common problem with EMG electrodes. As the residuum 7012 morphs or the patient puts loads on the residuum 7012, the pressure applied to each bladder 7028 by the residuum 7012 may vary, which in turn may vary the EMG electrodes' contact with the skin of the residuum 7012. The pressure sensors sense this pressure differential, and the control unit may adjust the pressure of the bladder(s) 7028 so as to put pressure back on the EMG electrodes 7060. This pressure on the EMG electrodes 7060 pushes the EMG electrodes 7060 against the skin of the residuum 7012, maintaining constant contact and a secure fit between the residuum and the support apparatus.

The control unit may include a partially-automatic control system for the actuator(s) 24 with preset actuator pressures. The user has a control unit 52 that can be programmed with preset numbers or modes that correspond to preset actuator pressures. These presets can be programmed by the patient while using the support apparatus 10 or can be pre-programmed. The preset pressures may be set to accommodate support apparatus fits for a resting mode, a light load mode, a high load mode, a massage mode, or other types of activity. Depending on the patient's activity, the patient selects a number or mode on the control unit 52, which automatically adjusts the fit and pressure of the actuator(s) 24 to whatever pressure(s) was programmed to that number. The massage mode may be utilized to facilitate circulation in the residuum. For example, the controller may turn off one actuator 24 at a time to allow blood flow into the region of the turned off actuator 24. By cycling through the actuators one at a time, blood flow in the residuum 12 is assisted, without loss of stability of the dynamic support apparatus 10.

The temperature control mechanism 19 of the dynamic support apparatus 10 may include the apertures 20 of the support apparatus 10 in FIG. 2. The apertures 20 allow for cooling by ventilation, which reduces moisture and heat between the support apparatus 10 and the residuum 12. Additionally, the temperature control mechanism 19 may include ducted air flow over the skin of the residuum 12, heat exchangers, personal cooling systems (such as those found in Sharper Image's "Personal Cooling System"), ducted fans, or integrating sports or outdoor recreation clothing designed for heat/moisture management. The temperature control mechanism 19 may be placed in a separate layer between the dynamic interface 16 or top surface 22 and the residuum 12, integrated into the same layer as the dynamic interface 16, or integrated into the top surface 22 of the frame 14. An active control system, similar to the system already described, may also be used to control the temperature control mechanism 19 so as to maintain a constant temperature, through the use of temperature sensors, between the residuum 12 and the support apparatus 10.

Figure 25:
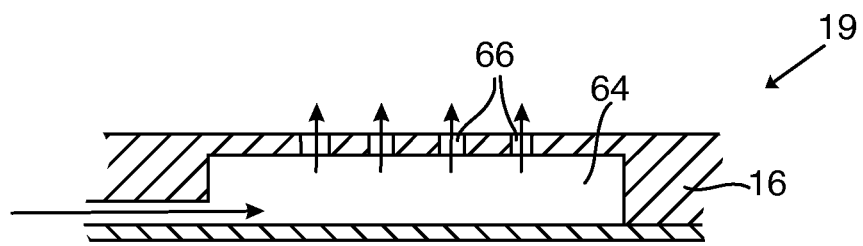
FIG. 25 is a cross-sectional view of one embodiment of a temperature control system of a dynamic support apparatus.

Referring to FIG. 25, the temperature control mechanism 19 may include one or more duct(s) 64 connected to a plurality of orifices 66 and integrated into the dynamic interface 16. In this embodiment, temperature control is accomplished by supplying air through the duct(s) 64 and the plurality of orifices 66 to impinge on the skin of the residuum.

Figure 27:
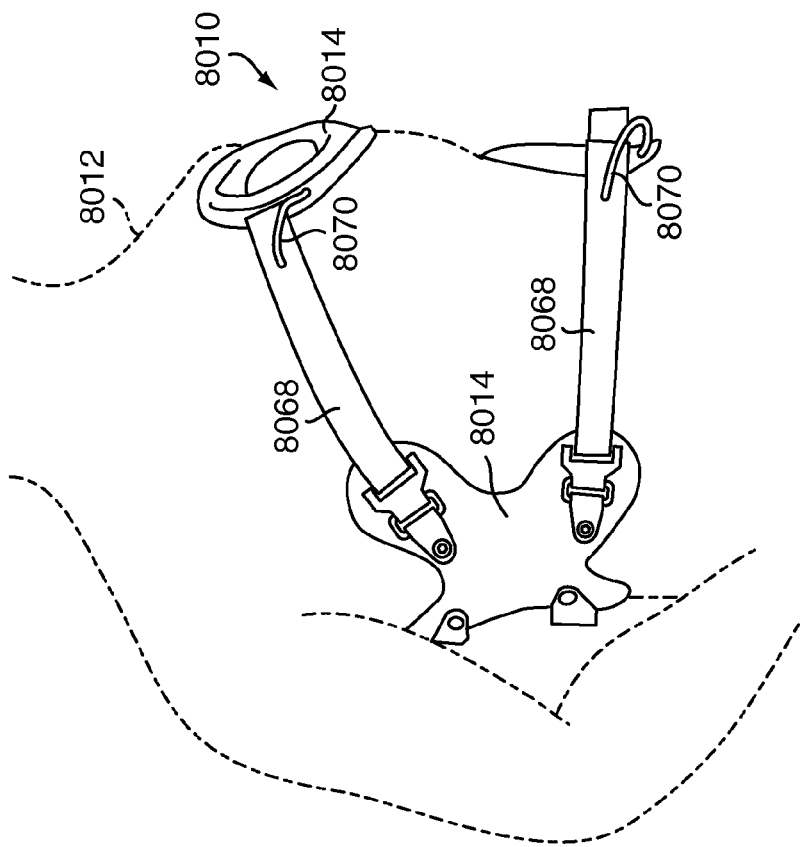
FIG. 27 is a side view of the dynamic support apparatus of FIG. 26.
Figure 26:
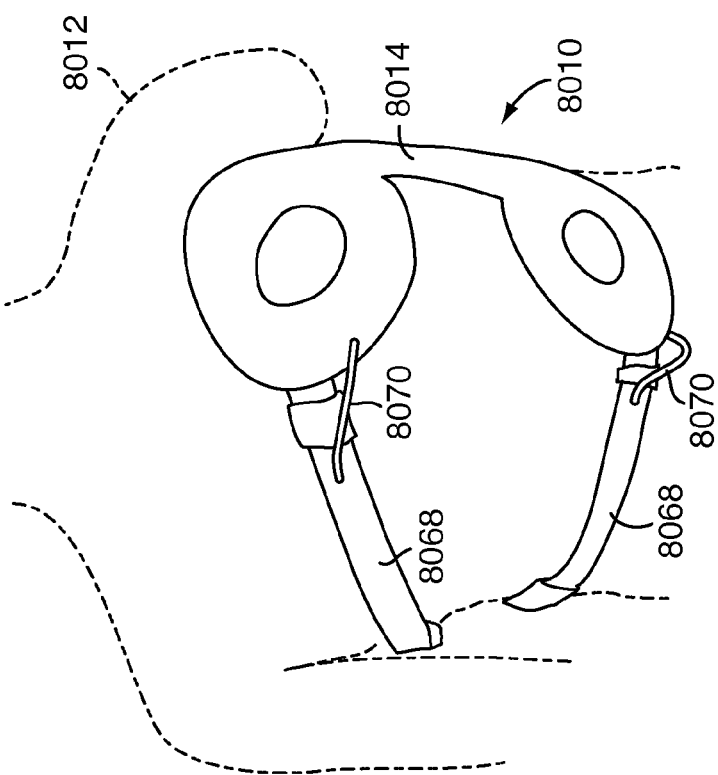
FIG. 26 is a front view of an alternative embodiment of a dynamic support apparatus as it is worn around die body.

While the exemplary embodiment described above relates to upper-limb prosthesis for TH amputees, the support apparatus can be used for transradial (TR) amputees and for shoulder disarticulation (SD) amputees. Referring now to FIGS. 26-28, one embodiment of a dynamic support apparatus 8010 for SD amputees includes a frame 8014, having actuators 8024 and connectors 8026, connected to one or more active straps 8068, such as McKibben artificial muscles. Each active strap 8068 contains at least one actuator and at least one strap connector 8070 for connecting the actuator to the control system. Similar to those embodiments already described, each active strap 8068 may also contain sensors and feedback loops for providing fit information to the control system. The active straps are connected to the control system and control unit. Thus, as pressure and tension on the active strap(s) 8068 change due to load variations on the residuum 8012, the sensors signal the control unit to adjust the pressure of the strap(s)'s actuator(s), which in turn adjusts the tension and length of the strap. These adjustments ensure a secure fit against the user's body and ensure stability of the prosthesis. The active straps 8068 and strap connectors 8070 may be integrated with the dynamic interface 8016, such that one control system controls both the dynamic interface 8016 and the active straps 8068 simultaneously. As should be understood by those skilled in the art, the strap connectors 8070 may alternatively be routed to a separate control unit specifically for the active straps 8068.

Referring to FIG. 28, in addition to controlling the tension and length of active straps 8068 by actuators, each active strap 8068 may additionally contain a length adjuster 8072, which may be used to manually adjust the length and fit of each active strap 8068.

Referring to FIGS. 29 and 30, in the exemplary embodiment having bladders 8028 for actuators 8024 and fluid path connectors 8030 for strap connectors 8070, the bladder 8028 is encased in a deformable strap material 8074, such as nylon webbing. The bladder 8028 is connected to the control system by the fluid path connector 8030. The end of each active strap 8068 has an attachment mechanism 8076 for attaching the active strap 8068 to the frame. The active strap 8068 is in a preset condition in FIGS. 29 and 30, having a strap length 8078 and a preset bladder cross-section.

Referring to FIGS. 31 and 32, the active strap 8068 is in an actuated condition having an actuated bladder cross section and an actuated strap length 8080 that is less than the preset strap length shown in FIG. 29. Accordingly, when instability is detected in the support apparatus, either by the control system or by the user, pressure may be increased in the active strap 8068, causing the bladder 8028 to expand from the preset condition of FIGS. 29 and 30 to the actuated condition of FIGS. 31 and 32. As pressure increases in the bladder 8028, the deformable strap material 8074 deforms, decreasing the length of the active strap 8068 and increasing stability in the support apparatus.

Figure 33:
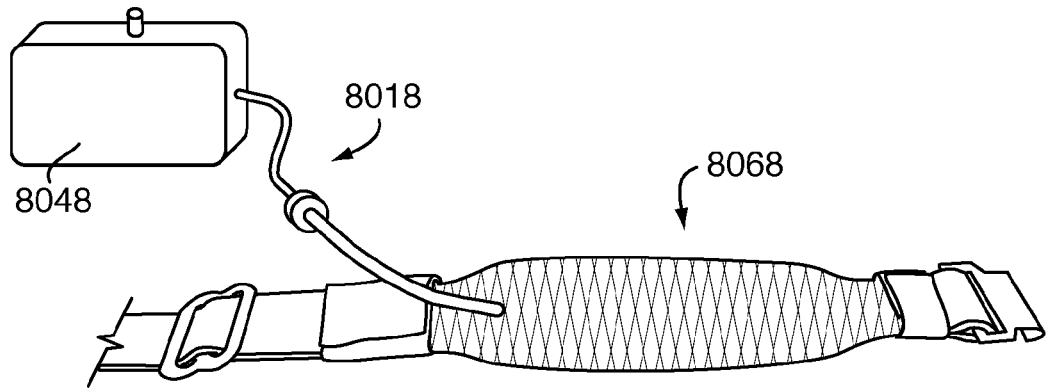
FIG. 33 is a perspective view of one embodiment of an active strap and control system of a dynamic support apparatus.

Referring to FIG. 33, the control system 8018 of each active strap 8068 may be an electric pump 8048, such that the pressure in each active strap 8068 may be adjusted independent of the other active straps 8068 and the dynamic interface.

Figure 34:
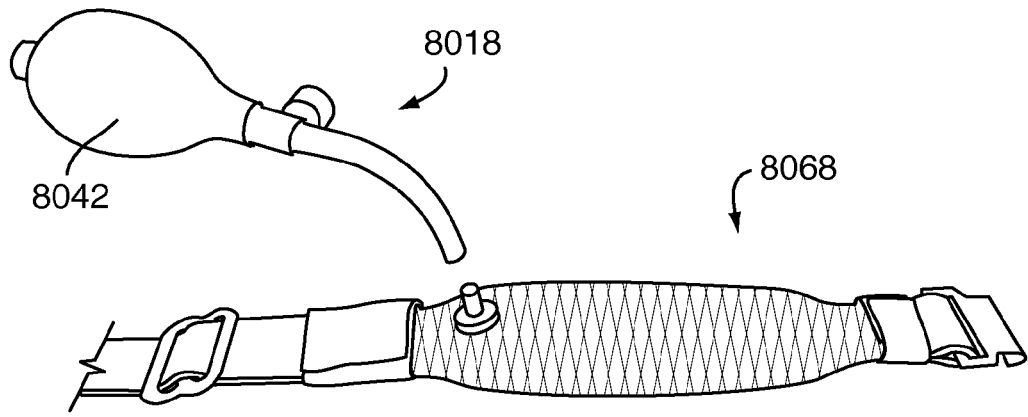
FIG. 34 is a perspective view of an alternative embodiment of an active strap and control system of a dynamic support apparatus.

Referring to FIG. 34, the control system 8018 of each active strap 8068 may alternatively be a pressure bulb 8042, such that the pressure in each active strap 8068 may be adjusted independent of the other active straps 8068 and the dynamic interface. Although shown as separate units in FIGS. 33 and 34, the control system 8018 may be integrated with the bladder 8028 similar to that shown in FIGS. 20 and 21.

Unlike typical McKibben artificial muscles, which are used in high-pressure applications, the active straps 8068 in the dynamic support apparatus 8010 are operated under low-pressure conditions. Accordingly, various configuration changes have been made to the inflation, arrangement and strap characteristics of the active straps 8068 to increase performance and efficiency in low-pressure conditions. The actuator length to strap length for the active strap 8068 is about two-thirds the length seen in the prior art. This increases actuation with less pressure, and makes the active strap 8068 and the support apparatus more responsive. Additionally, when the actuator in active strap 8068 is a bladder 8028, it may be fabricated wider than the strap itself so that the bladder 8028 can be inflated, causing the strap diameter to increase, without putting energy into stretching the bladder 8028 itself. Bladders that are fabricated by laser welding, such as the bladder 28 shown in FIG. 15, also provide for improved performance in low-pressure conditions because they can be constructed to deform the active strap 8068 in specific shapes and locations, rather than only circular deformation.

Figure 50:
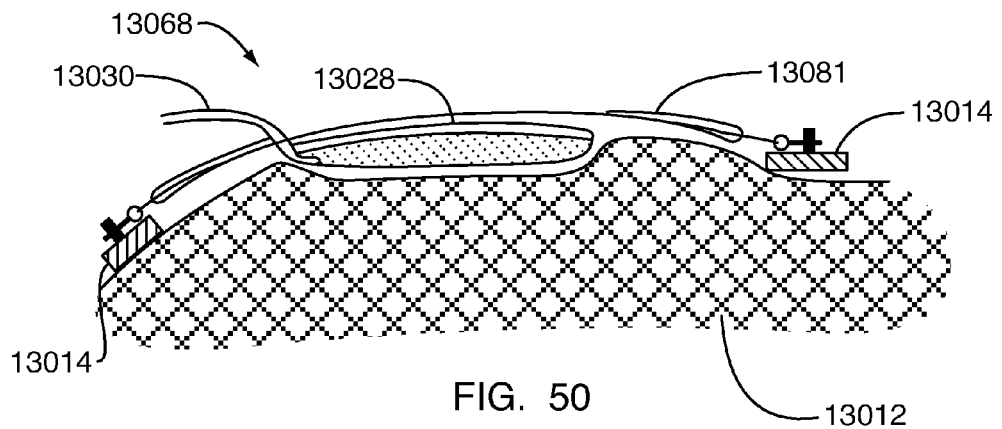
FIG. 50 is an illustrative view of a strap according to one embodiment.
Figure 51:
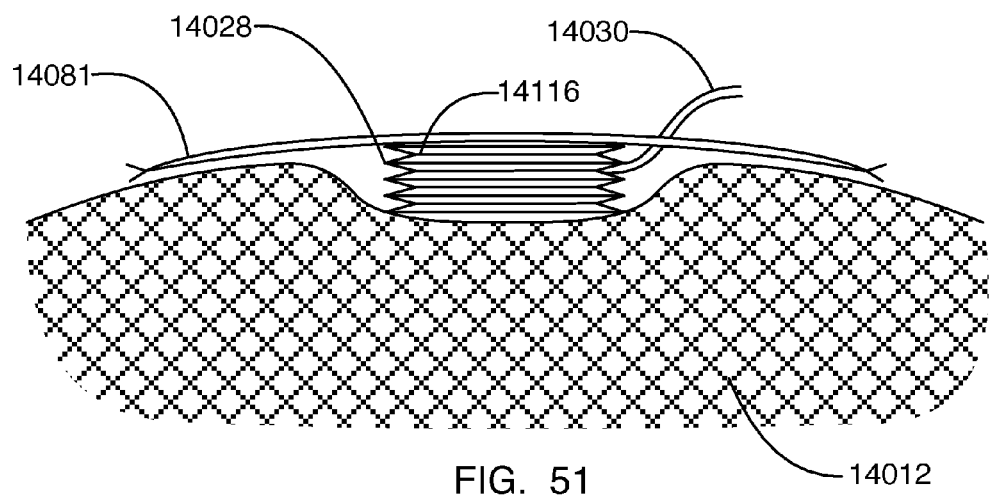
FIG. 51 is an illustrative view of a strap according to one embodiment.

Referring to FIG. 50, an additional embodiment of an active strap 13068 is shown. The active strap 13068 may include a flexible strap portion 13081 having a bladder 13028 attached thereto. The active strap 13068 is connected to the frame 13014 to secure the frame to the user's residuum 13012. For example, the active strap 13068 may secure a trans-radial prosthetic support to the user's elbow. The bladder 13028 is operatively connected to the control system 18, shown in FIG. 1, through a fluid path connector 13030. In operation, the active strap 13068 secures the frame 13014 to the residuum 13012, with the flexible strap portion 13081 providing the active strap 13068 with strong tensile strength. The bladder 13028 of the active strap 13068 may then be actuated while the frame is secured to the residuum 13012 to generate a normal force on the residuum 13012 to alter the securing properties of the active strap 13068. Thus, the bladder 13028 allows for remote adjustment of the fit of the support apparatus 10, shown in FIG. 1. The bladder 13028 also provides the active strap 13068 with a measure of compliance and may aid in anchoring the frame 13014 to the residuum, i.e., to prevent sliding. Although the bladder 13028 is shown in a particular embodiment for exemplary purposes, it should be understood that the bladder 13028 may be in the form of any of the various embodiments described herein. For example, as seen in FIG. 51, the bladder 14028 may include an accordion sidewall 14116 to allow for increased actuation.

Figure 35:
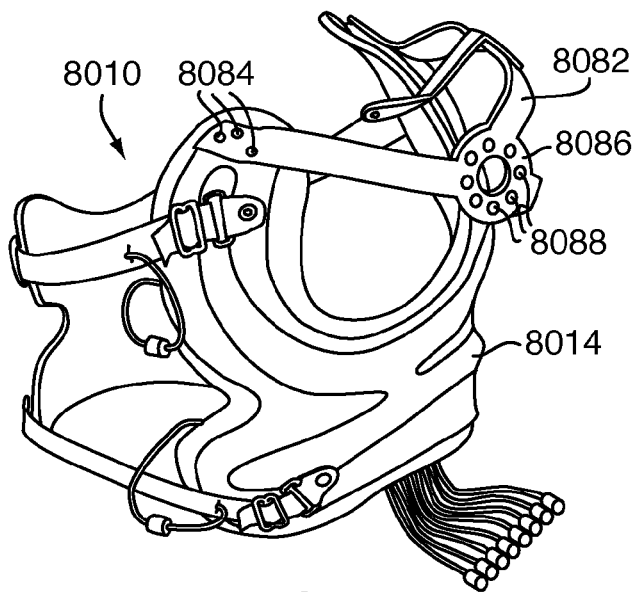
FIG. 35 is a front perspective view of one embodiment of a dynamic support apparatus showing a prosthetic interface.
Figure 38:
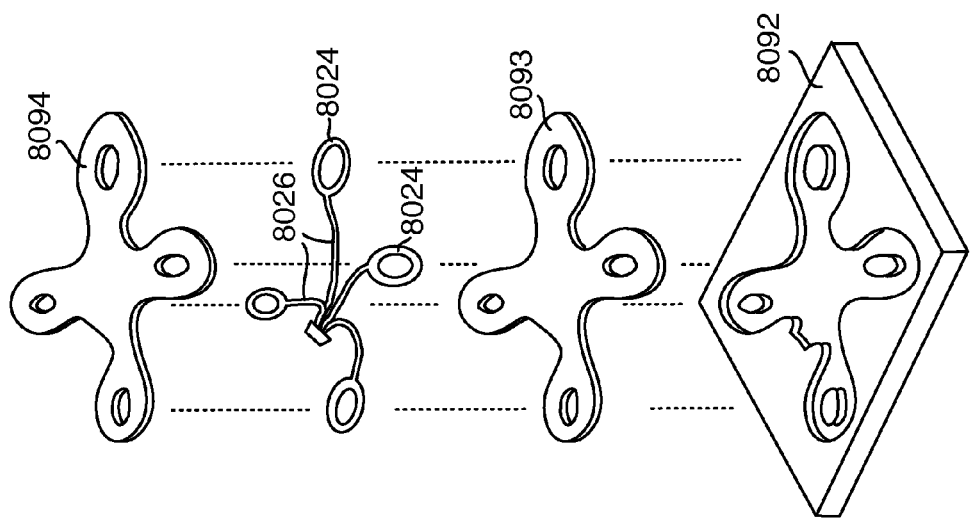
FIG. 38 is an illustration of a portion of the technique for fabricating and embodiment of a dynamic interface for a dynamic support apparatus.
Figure 37:
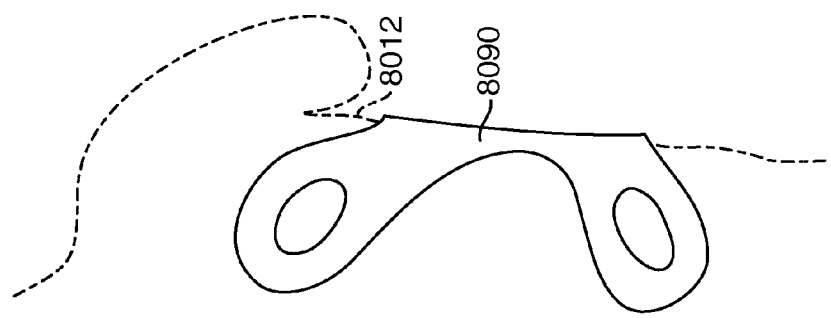
FIG. 37 is an illustration of a portion of one technique for fabricating and embodiment of a dynamic interface for a dynamic support apparatus.
Figure 36:
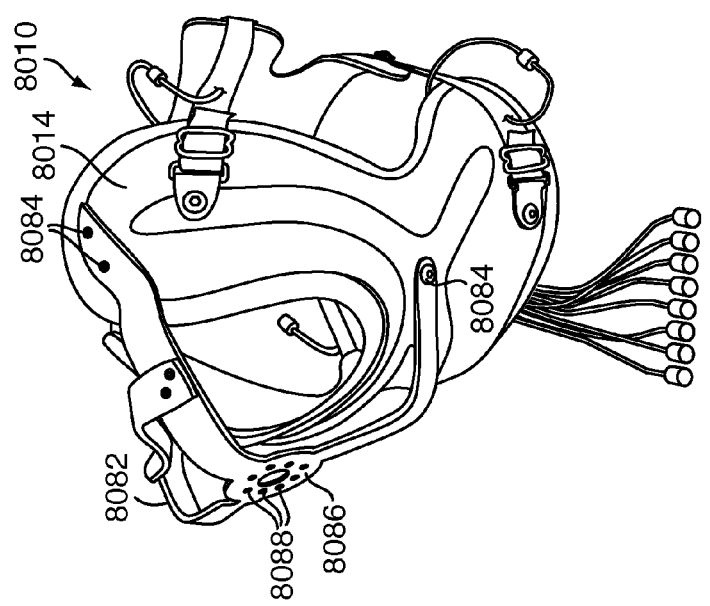
FIG. 36 is a rear perspective view of the dynamic support apparatus of FIG. 35.
Figure 40:
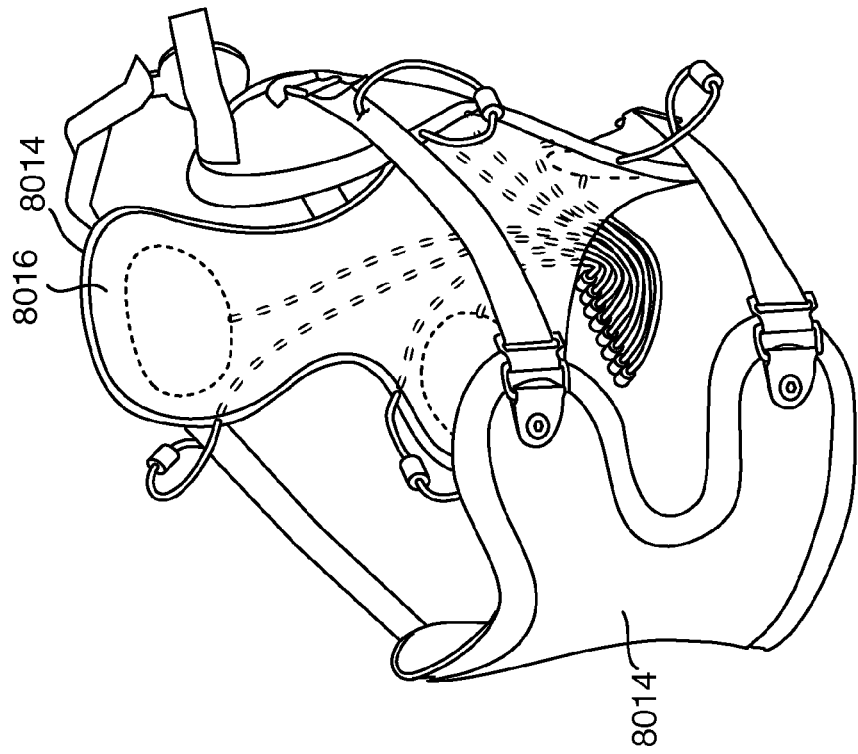
FIG. 40 is a front perspective view of the dynamic support apparatus of FIGS. 37-39.
Figure 39:
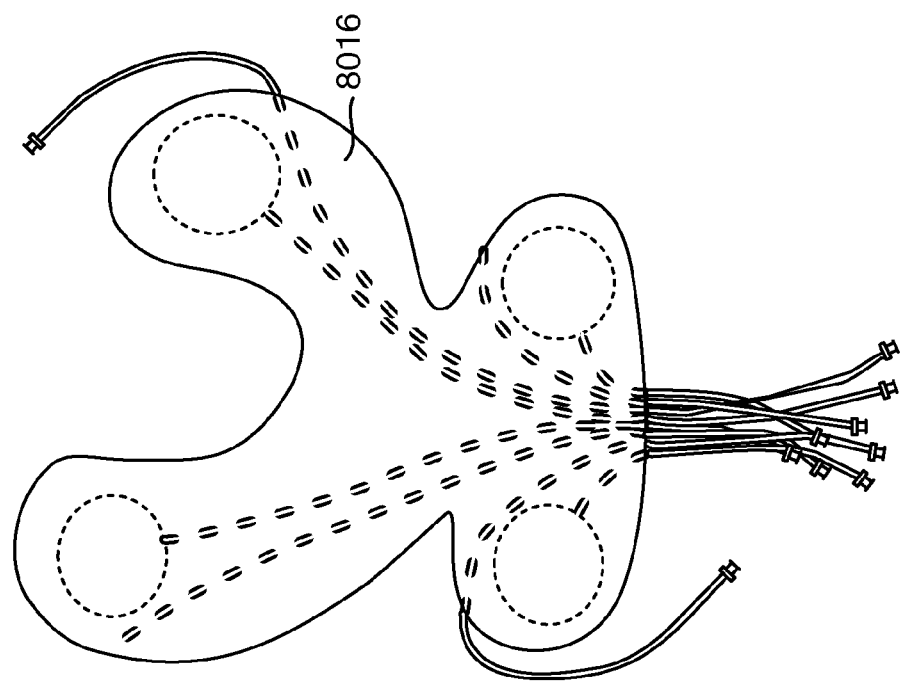
FIG. 39 is a front view of the dynamic interface fabricated from the technique of FIGS. 37 and 38.
Figure 42:
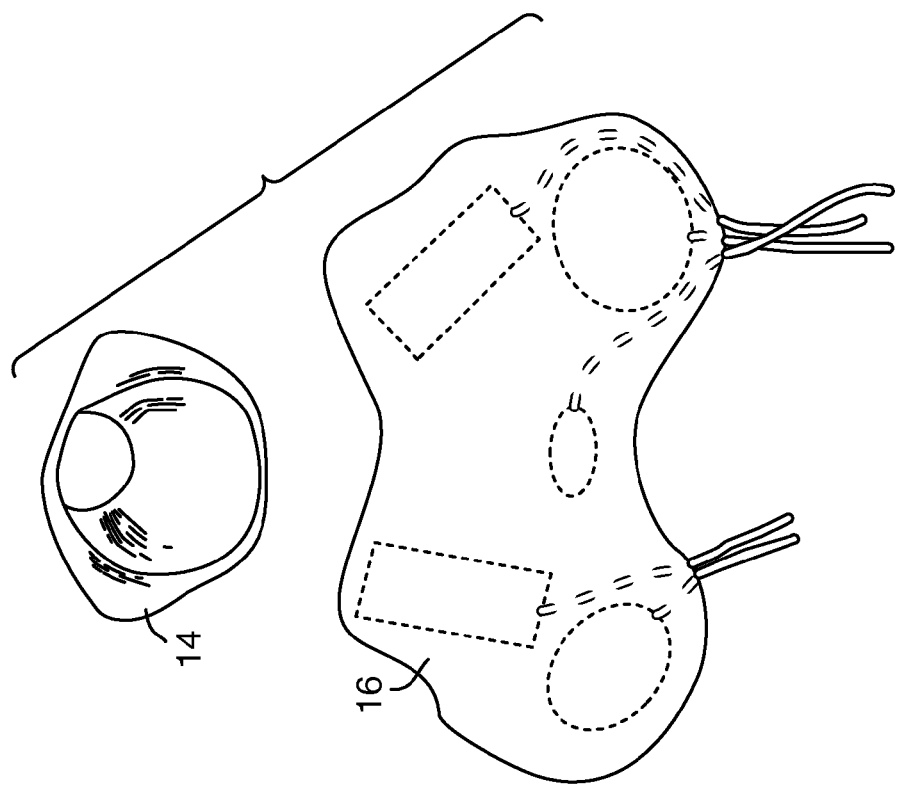
FIG. 42 is a front view of an alternative embodiment of a dynamic interface fabricated from the technique of FIGS. 37 and 38.
Figure 41:
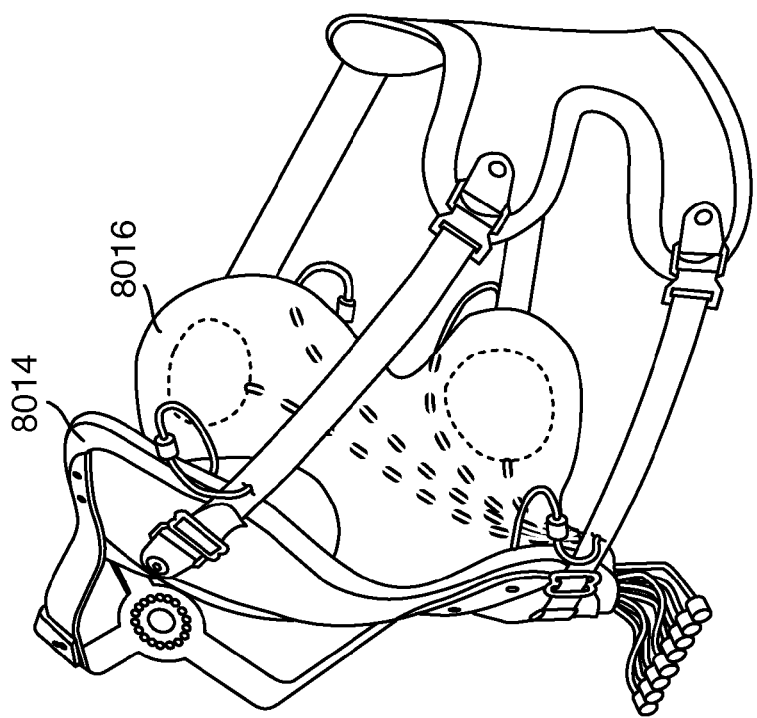
FIG. 41 is a rear perspective view of the dynamic support apparatus of FIGS. 37-39.
Figure 45:
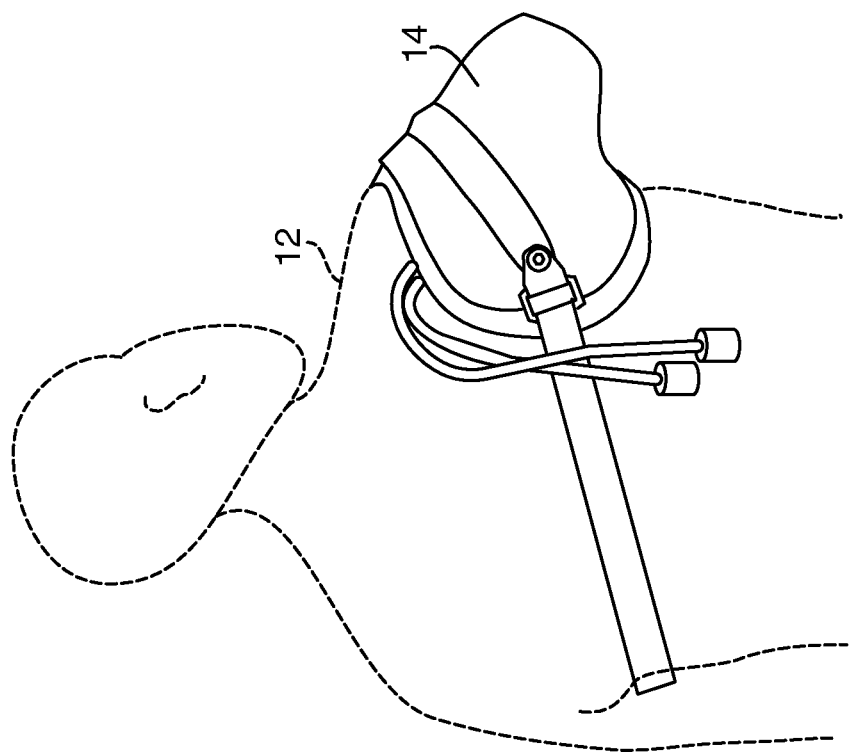
Figure 44:
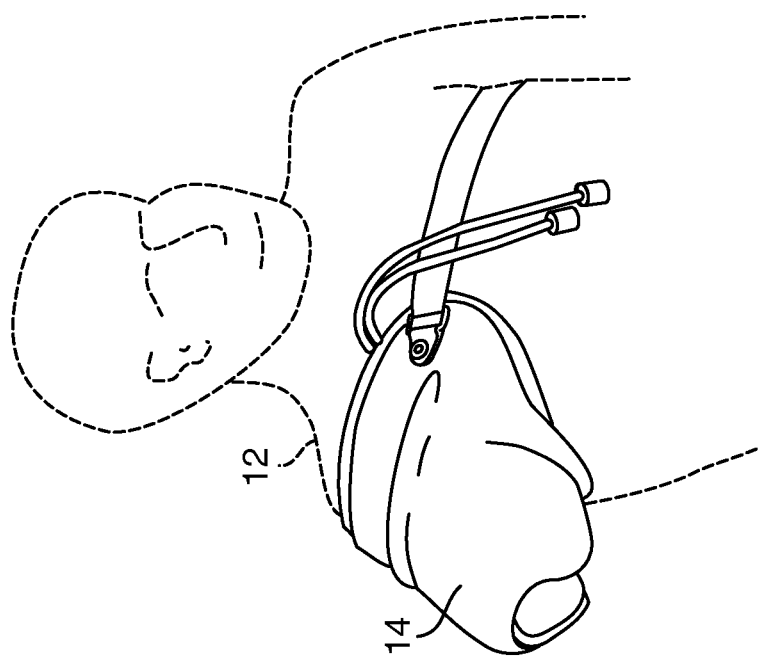
FIG. 44 is a front perspective view of the dynamic support apparatus of FIG. 43 as worn by a patient.
Figure 48:
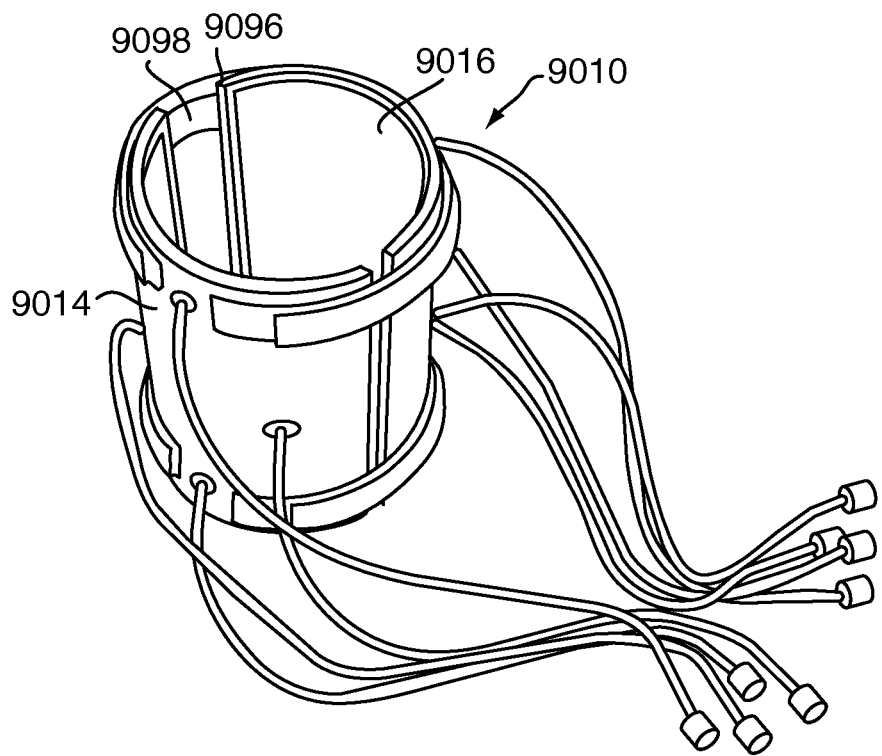
FIG. 48 is a perspective view of the dynamic support apparatus of FIG. 46.
Figure 49:
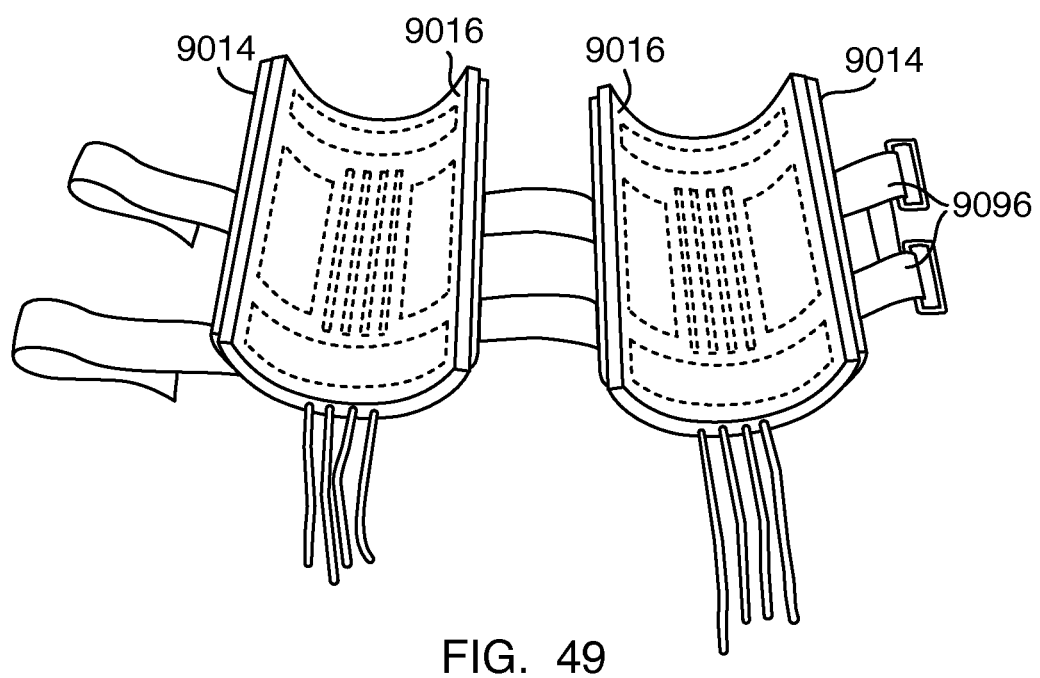
FIG. 49 is a side view of the dynamic support apparatus of FIG. 46 when completely opened.

Referring to the embodiment shown in FIGS. 35 and 36, attached to the support apparatus 8010 is a prosthetic interface 8082 for attaching a prosthesis (not shown) to the support apparatus 8010. The prosthetic interface 8082 is fixedly attached to the support apparatus 8010 by attachment means 8084, which may be rivets, bolts or any similar means of attachment. The prosthetic interface 8082 has a prosthetic mount 8086 for to which the prosthesis may be attached. The prosthetic mount 8086 preferably includes a standard coupling configuration to facilitate attachment of the prosthesis. Although shown as holes 8088, it should be understood that the standard coupling configuration could also be a bolt configuration that interfaces with corresponding holes on the prosthesis. The prosthetic interface 8082 should be rigid in construction, such that it does not bend or flex when the attached prosthesis is used to lift a heavy object.

Referring to FIGS. 37-41, a method of fabricating the dynamic interface of the dynamic support apparatus may be a layer molding technique. For example, for the SD prosthesis support apparatus 8010, such method may involve the steps of scanning the contour of a patient's residuum 8012 in an outline 8090 where the frame will sit on the residuum 8012; flattening the scanned contour so that it can be made into a template for a mold 8092; machining the "flattened" template into the mold 8092; pouring silicone or similar material in the mold 8092 to half the final thickness of the dynamic interface 8016 to create a first interface layer 8093; laying the actuator(s) 8024 and connector(s) 8026 on top of the first interface layer 8093; pouring silicon or similar material on top of the actuator(s) 8024 and connector(s) 8026 to a desired thickness of the dynamic interface 8016 to create a second interface layer 8094; removing the resulting dynamic interface 8016 from the mold 8092; and connecting the resulting dynamic interface 8016 to a control system (not shown) and a frame 8014.

Although described with regard to the SD prosthesis support 8010, as seen in FIGS. 42-45, the dynamic interface 16 fabricated by the layer molding technique described above can also be applied to other types of prosthesis support apparatuses by scanning the appropriate part of the residuum 12 and attaching the resulting dynamic interface 16 to the frame 14 and control system.

An alternative method of fabricating a dynamic interface, for example for a TH prosthesis support apparatus, may involve the steps of scanning the contour of a patient's residuum to form an inner mold of the TH residuum; forming the inner mold of the TH residuum; coating the inner mold with an inner layer of liner made of material such as silicon or similar material; scanning the inner mold to generate an outer mold; forming an outer mold; laying the actuator(s) 24 and connector(s) 26 on top of the inner layer of liner; pouring an outer layer of silicon or similar material on top of the inner layer, the actuator(s) 24, and the connector(s) 26; using the outer mold to form the outer layer of the dynamic interface 16; and connecting the resulting dynamic interface 16 to a control system 18 and a frame 14.

Referring back to FIG. 22, the frame 7014 may be capable of expanding or opening to facilitate donning and doffing the support apparatus. One or more securing mechanisms 7096, such as snaps or latches, may be used to prevent expansion or opening of the frame 7014 while the support apparatus 7010 is being worn by the user.

Referring to FIGS. 46-49, in an alternative embodiment, the support apparatus 9010 may be capable of expanding or opening parallel to its longitudinal axis to facilitate donning and doffing. An opening 9098 of the frame 9014 may run along only a portion of the length of the support apparatus 9010 or may run along the entire length of the support apparatus 9010 from the proximal to the distal end of the apparatus. The securing mechanism 9096, such as a circumferential straps, may be used to prevent expansion or opening of the frame while the support apparatus is being worn by the user. In this embodiment, the dynamic interface 9016 may be composed of multiple portions, each being attached to a part of the frame 9014.

Some embodiments may also include an exhaust system that is incorporated into the control system. The exhaust system may channel excess fluid resulting from the release of pressure in the actuators to one or more exhaust outlets. In the exemplary embodiment, with air as the fluid, the exhaust outlets may vent the air into the atmosphere. In other embodiments, the exhaust outlets may channel the air into a reservoir, from which the fluid can be drawn back into the system to increase pressure. These exhaust outlets may also be strategically positioned or ducted along the frame to channel flow over the surface of the residuum. This flow could aid convective cooling of the residuum.

The dynamic interface is able to change geometry to provide a fit with the residuum 12. The user may manually actuate the dynamic interface to increase stability as needed. The dynamic support apparatus 10 may include a temperature control system to increase the comfort of the dynamic support apparatus. The frame may be capable of opening to assist the user in donning and doffing the dynamic support apparatus.

The control system may actively actuate the dynamic interface based on fit information provided by sensors. The control system may include preset modes such that the fit may be changed for each mode. The control system may include a massage mode for increasing blood circulation in the residuum.

Figure 52:
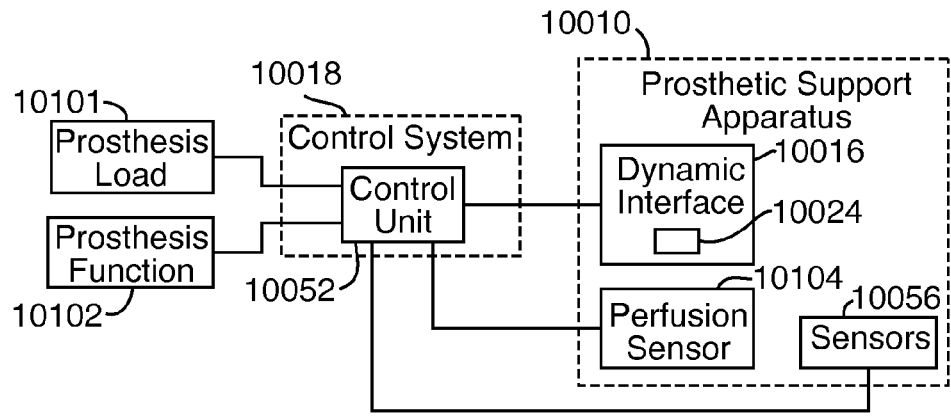
FIG. 52 is a schematic diagram of the prosthetic support apparatus according to another embodiment of the present invention.

Referring to FIG. 52, in some embodiments, the prosthesis (not shown) itself may send signals to the control unit 10052 of the active control system 10018 so that the control unit 10052 may adjust the dynamic interface 10016 of the support apparatus 10010 based on the current usage of the prosthesis (not shown). For instance, the prosthesis (not shown) may send load signals 10100 indicative of the loading of the prosthesis (not shown). The load signals 10100 may be provided to the control unit 10052 by force sensors, compliance sensors and/or motors within the prosthesis (not shown). The prosthesis (not shown) may also send function signals 10102 to the control unit 10052 indicative of a mode of operation of the prosthesis (not shown) and/or of a current positioning of the prosthesis (not shown). The load signals 10100 and the function signals 10102 may be transmitted to the control unit 10052 through a wired connection or wirelessly, for example, through Bluetooth, radio or the like.

The load signals 10100 and the function signals 10102 allow the control system 10018 to actively alter the type and level of support provided to the prosthesis (not shown) by the support apparatus 10010. For example, the control unit 10052 may compensate for load signals 10100 indicating high loading of the prosthesis (not shown) by increasing the actuation of the actuators 10024 of the support apparatus 10010 to better secure the support apparatus 10010 to the residuum 12, shown in FIG. 1. Similarly, the control unit 10052 may compensate for load signals 10100 indicating low loading of the prosthesis (not shown) by decreasing the actuation of the actuators 10024 to loosen the interface between the support apparatus 10010 and the residuum 12, shown in FIG. 1. Thus, the control unit 10052 is able to provide increased support to the prosthesis (not shown) when necessary and to loosen the support to allow for improved blood circulation in the residuum, shown in FIG. 1, during lower loading conditions. The function signals 10102 may also provide improved control to the prosthetic support apparatus 10010. For instance, the function signals 10102 may indicate a current mode of operation of the prosthesis (not shown), which may allow the control unit 10052 to alter the support provided by the support apparatus 10010 to suit the operating mode. For example, if the function signal 10102 indicates that the prosthesis (not shown) has entered a standby mode, the control unit 10052 may decrease actuation of the actuators 10024 or enter a massage mode to increase blood circulation in the residuum 12, shown in FIG. 1. Additionally, the function signals 10102 may provide information to the control unit 10052 indicating a current position of the prosthesis (not shown), for example, through position sensors such as potentiometers, magnetic sensors, Hall effect sensors and the like. Using these function signals 10102, the control unit 10052 may actuate specific actuators 10024 more than others to provide greater support in certain areas of the support apparatus 10010 based on the position of the prosthesis (not shown). Thus, the load signals 10100 and the function signals 10102 may provide for improved active control of the prosthetic support apparatus 10010 based on detected function or loads that the prosthesis (not shown) is imparting on the support apparatus 10010 so that the support apparatus 10010 may adjust appropriately.

Figure 53:
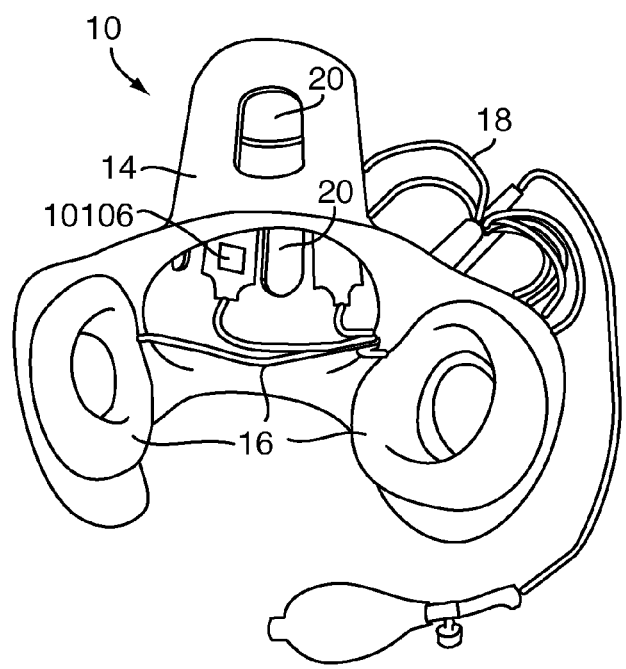
FIG. 53 is a perspective view of the prosthetic support apparatus of FIG. 52.

In various embodiments, the support apparatus 10010 may additionally include perfusion sensors 10104, in communication with the control unit 10052, to determine the amount of blood flowing in tissue of the residuum 12, shown in FIG. 1, underneath the areas of contact with the actuators 10024. For example, referring to FIG. 53, in some embodiments, the perfusion sensor 10104 may be a pulse oximeter 10106 for detecting whether or not the skin is adequately perfused. In other embodiments, the perfusion sensor 10104 may be a blood volume pulse sensor for detecting blood flow within the residuum 12, shown in FIG. 1. If the skin is not, the control unit 10052 may decrease actuation of one or more of the actuators 10024 and enter a massage mode to increase blood circulation in the residuum 12, shown in FIG. 1.

Referring to FIGS. 54-56, in some embodiments, the support apparatus 10, shown in FIG. 1, may include bladders 11028 having a lateral stabilization system 11108. The lateral stabilization system 11108 includes a base plate 11110 and a cover plate 11112 having the bladder 11028 disposed therebetween. The base plate 11110 may be fixedly secured to the frame 11014 of the support apparatus 10, shown in FIG. 1. The base plate 11110 and the cover plate 11112 are pivotally connected to each other by a linkage 11114, which is preferably a four bar linkage, as seen in FIG. 55A. The linkage 11114 substantially prevents the cover plate 11112 from moving in the lateral direction L relative to the base plate 11110, while allowing the cover plate 11112 to pivot in the transverse direction T away from and back toward the base plate 11110, as seen in FIG. 56. The bladder 11028 may include an accordion sidewall 11116 to provide an increased actuation distance D that the cover plate 11112 may be actuated away from the base plate 11110, and the lateral stabilization system 11108 ensures that lateral stability is not lost as the bladder 11028 actuates to the increased actuation distance D.

The cover plate 11112 preferably includes a residuum contact surface 11118 that is contoured to improve user comfort, for example, by providing rounded corners 11120 that will not dig into the residuum 12, shown in FIG. 1. In other embodiments, the contact surface 11118 may be contoured to the shape of the user's residuum to increase comfort. Referring to FIG. 54, the cover plate may also include one or more sensor cavities 11122 for accommodating one or more sensors 11056 for monitoring the fit of the support apparatus 11010 and/or the condition of the residuum 12, shown in FIG. 1. The sensors 11056 may be, for example, force sensors, pressure sensors, temperature sensors, perfusion sensors or the like. Preferably, the base plate 11110 and the cover plate 11112 are also formed to improve user comfort, for example by being formed from a lightweight material such as an open-cell foam.

Figure 57:
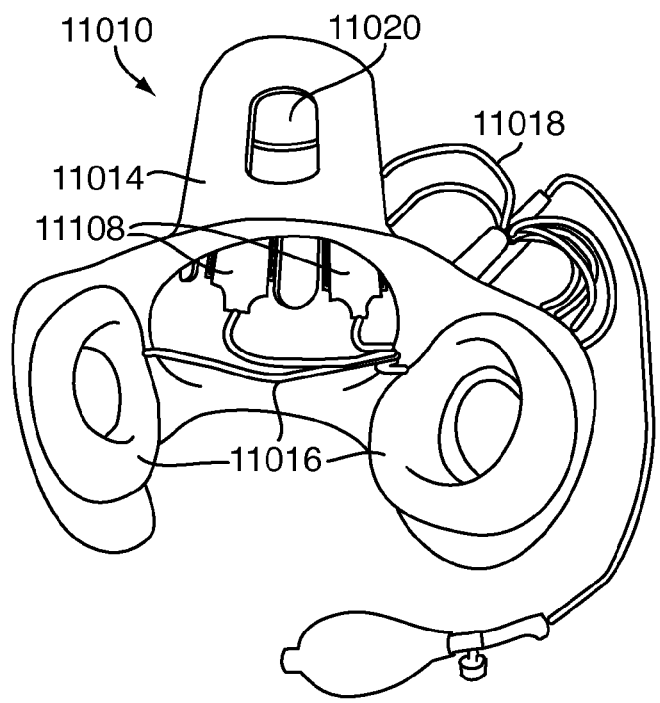
FIG. 57 is a perspective view of an embodiment of a prosthetic support apparatus including the laterally stabilized bladder of FIG. 54.

Referring to FIG. 57, the bladders 11028 having the lateral stabilization systems 11108 may be arranged around the support apparatus 11010 in a manner similar to those discussed above.

Figure 58:
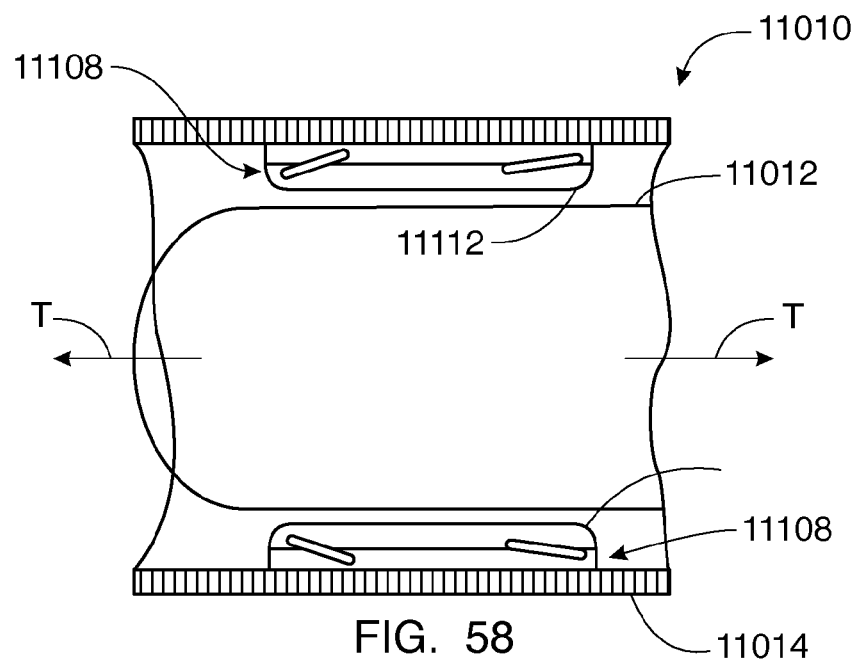
FIG. 58 is a cross-sectional view of the prosthetic support apparatus of FIG. 57 in an inactuated state with a residuum inserted therein.

Referring to FIG. 58, in operation, the user may insert their residuum 11012 into the support apparatus 11010 in the transverse direction T, while the bladders 11028, shown in FIG. 55, having the lateral stabilization systems 11108 are in an inactuated state. Since the lateral stabilization system 11108 provides for the increased actuation distance D, shown in FIG. 55, when inactuated, the cover plate 11112 may be completely out of contact with the residuum 11012. Thus, the user may insert their residuum 11012 easily, without a mushrooming of the soft residuum tissue that may be caused by contact with the support apparatus 11010. Then, referring to FIG. 59, the bladders 11028 may be actuated, causing them to expand. As the bladders 11028 expand, they push the cover plates 11112 away from the base plates 11110. The linkage 11114 connecting each cover plate 11112 to each base plate 11110 pivots to allow the cover plate 11112 to move away from the base plate 11110, while maintaining lateral stability. The cover plates 11112 are actuated into contact with the residuum 11012 to secure the support apparatus 11010 to the residuum 11012. To remove the support apparatus 11010, the bladders 11028 may simply be returned to their inactuated states, as seen in FIG. 58, and the residuum 11012 may be withdrawn from the support apparatus 11010.

The lateral stabilization system 11108 is advantageous because in prevents unintentional removal of the residuum 11012 from the support apparatus 11010, for example, due to slippage or the like. Specifically, if the residuum 11012 begins to move in the transverse direction T while the bladders 11028 are actuated and in contact with the residuum 11012, the movement will create a camming effect, pulling on the cover plate 11112 and causing the cover plate 11112 to pivot further away from the base plate 11110. As the cover plate 11112 moves further from the base plate 11110, the contact force against the residuum 11012 is increased, securing the support apparatus 11010 more tightly thereto. Thus, the laterally stabilized bladders 11028 provide an improved securing interface when actuated, yet also allow for ease of donning and doffing when inactuated, as discussed above.

Referring to FIG. 60, in some embodiments, the lateral stabilization system 11108 may be provided with one or more resilient members 11124 connecting the cover plate 11112 to the base plate 11110 and applying a compressive force therebetween. For example, the one or more resilient members 11124 may be elastic members, spring members or the like. The one or more resilient members 11124 ensure that the cover plate 11112 pivots back into contact with the base plate 11110 when in an inactuated state.

Although described in connection with the exemplary embodiment, it should be understood that various changes to the bladders 11028 and lateral stabilization system 11108 may be made. For example, in some embodiments, the bladder 11028 may be anchored directly to the support apparatus 11010, eliminating the need for the base plate 11110. In this embodiment, the linkage 11114 may be pivotally connected directly to the support apparatus 11010. In some embodiments, rather than the bladder 11028 with accordion sidewall 11116, two or more bladders without accordion sidewalls may be arranged between the cover plate 11112 and the base plate 11110 to provide the increased actuation distance D. In other embodiments, the linkage 11114 may be telescopic, as seen in FIG. 60A, rather than pivotal, thereby providing stability in both the lateral and transverse directions. Additionally, although each bar of the linkage 11114 is shown as being substantially the same length, the lengths may be varied to alter the configuration of the cover plate 11112 relative to the base plate 11110. For example, rather than being parallel to the base plate 11110, the cover plate 11112 may instead be angled to one side in the lateral direction L or angled to the front or back in the transverse direction T.

Figure 56A:
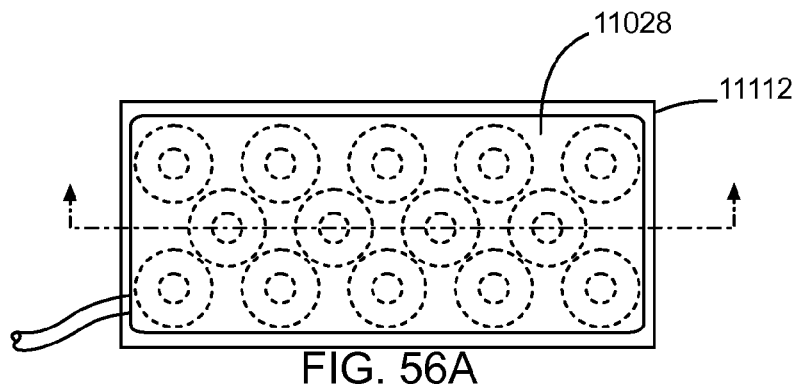
FIG. 56A is a top view of another embodiment of a laterally stabilized bladder.
Figure 56B:
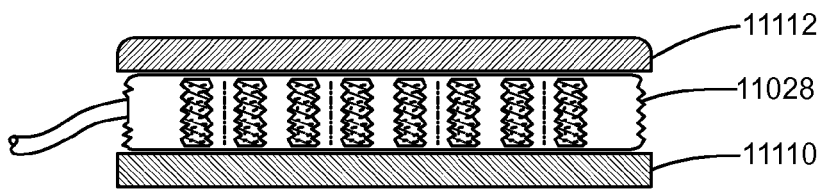
FIG. 56B is a cross-sectional view of the laterally stabilized bladder of FIG. 56A when unactuated.
Figure 56C:
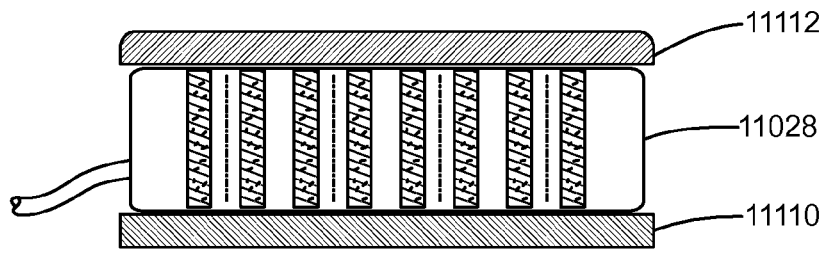
FIG. 56C is a cross-sectional view of the laterally stabilized bladder of FIG. 56A when actuated.
Figure 56D:
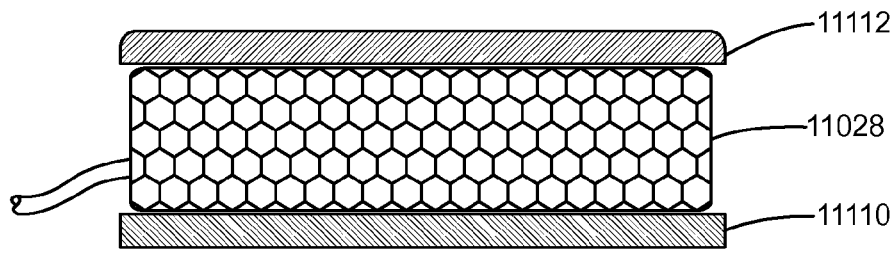
FIG. 56D is a cross-sectional view of another embodiment of a laterally stabilized bladder.
Figure 56E:
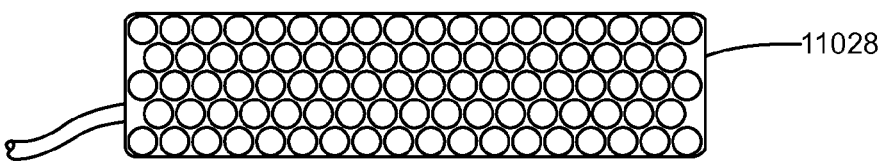
FIG. 56E is a cross-sectional view of another embodiment of a laterally stabilized bladder.

Although the lateral stabilization system 11108 has been described as surround the bladder 11028, referring to FIG. 56A-56E, in other embodiments, the bladder 11028 may include an open cell foam structure disposed inside the bladder 11028 to create internal struts and connectors, which are flat when the bladder 11028 is deflated. In operation, the bladder 11028 is anchored to the base plate 11110 or frame 11014. As the bladder 11028 inflates, the bladder 11028 the structure of the foam or material inside the bladder 11028 provides the bladder 11028 with lateral stability. In some embodiments, the open cell foam structure may be toroidal, as seen in FIGS. 56A-56C. In various other embodiments, a honeycomb or multi-tube structure may be introduced, as seen in FIGS. 56D and 56E, to provide greater lateral stability when the bladder 11028 is inflated.

In various embodiments, bladder inflation may be accomplished by introducing carbon dioxide ($CO_2$) into the bladder, rather than air. For example, referring to FIG. 61, the control system 12018 may include one or more $CO_2$ cartridges 12126. The $CO_2$ cartridges are advantageous because they may quickly fill the bladders 28, shown in FIG. 3. Additionally, the CO2 cartridges are themselves refillable, so they may simply be removed from the control system 12018 to be refilled or replaced. Inflation using the one or more $CO_2$ cartridges 12126 may also improve the temperature control mechanism 19, shown in FIG. 1, because the $CO_2$ may decrease in temperature as it expands to fill the bladders 28, shown in FIG. 3, thereby cooling the user where the user is in contact with the bladders 28.

Depending upon the degree of amputation of the user of the prosthetic arm, in some embodiments, it may be desirable to couple some degree of movement of the user's arm with a shortened prosthetic arm, for example, a prosthetic arm that provides only wrist flexion and hand movement capabilities. Thus, referring to FIG. 62, a trans-radial socket 13128 may be provided for trans-radial amputees that are still able to pronate and supinate their residuum (not shown). The trans-radial socket 13128 includes a bracket body 13130 connected to a cup brace 13132 by two hinged brackets 13134. The bracket body includes an outer cylinder portion 13136 attached to the hinged brackets 13134 and an inner tubular portion 13138 partially rotatably fixed within the outer cylinder portion 13136 and extending axially outward therefrom to a distal end 13140. In operation, the prosthetic arm (not shown) is mounted to the trans-radial socket 13128 at the distal end 13140 of the inner tubular portion 13138. The user may then insert their residuum into the inner tubular portion 13138. The cup brace 13132 may then be slid along their upper arm behind the user's elbow. The hinged brackets allow the user to bend their elbow to move the bracket body 13130. Additionally, the user may pronate and/or supinate their residuum, to rotate the inner tubular portion 13138 relative to the outer cylinder portion 13136, which in turn causes the prosthetic arm mounted to the inner tubular portion 13138 to rotate. Thus, the trans-radial socket 13128 provides for a reduction in the size of the prosthetic arm by eliminating the need for a wrist rotator for users having natural rotation capability in their residuum. This reduction in the size of the prosthetic arm results in a corresponding reduction in weight of the prosthetic arm, thereby improving user comfort. Additionally, the trans-radial socket 13128 eliminates the need for the prosthetic arm to provide wrist rotation, thereby making the prosthetic arm easier for the user to control by reducing the number of joint movements for which the user must learn new control inputs. Additionally, reducing the number of joint movements provided by the prosthetic device may also improve battery power usage and lead to extended battery life.

Referring to FIG. 63, an embodiment of a dynamic support system 142 is shown. In the dynamic support system 142, the dynamic support apparatus 10 is in communication with both the user's residuum 12 and the prosthesis 11 and is, therefore, able to vary its configuration as the state of the residuum 12 and/or the prosthesis 11 changes. For instance, as discussed above, the dynamic support apparatus 10 includes a variety of sensors for detecting the condition of the residuum, such as temperature sensors and perfusion sensors 10104, shown in FIG. 52. Additionally, as discussed above, the dynamic support apparatus may also receive prosthesis load information 10100 and prosthesis function information 10102, shown in FIG. 52, from the prosthesis 11. The dynamic support system 142 also includes a variety of interface sensors, such as pressure sensors 7056, shown in FIG. 22, detecting the condition of the interface between the residuum 12 and the dynamic support apparatus 10. Information from all of these various sensors and sources are used in the dynamic support system 142 to alter the state of the dynamic interface 16, thereby changing the fit of the dynamic support apparatus 10. The dynamic support system 142 may also include interface stimulators 144 to provide feedback to the user regarding the state of the dynamic interface 10. For instance, the dynamic support system 142 may use tactors 146 to provide vibration or other tactile feedback to the user. Additionally, the dynamic support system 142 may also include a variety of passive elements for improving comfort and fit of the dynamic support apparatus 10 and/or for communicating information to the user. For instance, the apertures 20 provide passive temperature control and the contact between the dynamic support apparatus 10 and the residuum 12 acts as a passive loading interface stimulator. Thus, the dynamic support system 142 provides beneficial integration between the dynamic support apparatus 10, the prosthesis 11 supported by the dynamic support apparatus 10 and the user.

The dynamic support apparatus is advantageous because it is able to compensate for shape changes of the residuum and/or loading from a prosthetic device by actuating the actuators. Additionally, when the actuators actuate, compliant tissue surrounding the bone within the residuum is displaced, thereby minimizing the amount of soft compliant tissue between the dynamic support apparatus and the bone within the residuum. This advantageously provides for a stronger interface between the dynamic support apparatus and the residuum. The dynamic support apparatus is also advantageous because various actuators may be actuated and unactuated at different times to improve blood flow within the residuum, without losing stability of the dynamic support apparatus.

The dynamic support apparatus is also able to advantageously detect the pressure and/or force provided by each actuator and to compensate for changes in the detected pressure and/or force. Thus, the dynamic support apparatus is able to self compensate for pressure and/or force changes to provide increased securing forces and tighten the dynamic support apparatus only when necessary and to loosen the dynamic support apparatus when the prosthetic device is under lower load. This minimizes the perceived weight of the prosthetic device, which may allow the user to adorn the prosthetic device and dynamic support apparatus for a greater time than with a conventional prosthesis.

Although the dynamic support apparatus is illustrated for use with an upper-limb prosthesis, the support apparatus is adaptable to other body appliances such as ski boots, shoes, backpacks, lower-limb prostheses, braces worn around a body part, or anything designed to be worn around a body part.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A dynamic support apparatus comprising:
    a frame having a surface, the frame configured to attach to a prosthetic device;
    a dynamic interface, capable of changing its geometry, disposed on the surface of the frame, the dynamic interface having a residuum contact surface and at least one actuator adapted to move the residuum contact surface relative to the surface of the frame; and
    a control system operably connected to the dynamic interface by at least one connector;
    wherein the control system controls actuation of the at least one actuator; and
    wherein the at least one actuator includes a lateral stabilization system allowing movement of the residuum contact surface in a first direction relative to the surface of the frame while preventing movement in at least a second direction perpendicular to the first direction.

2. The dynamic support apparatus according to claim 1 further comprising at least one sensor in communication with the control system for providing feedback signals to the control system.

3. The dynamic support apparatus according to claim 2 further comprising wherein the at least on sensor is disposed on the dynamic interface.

4. A dynamic support apparatus comprising:
    a frame having a surface, the frame configured to attach to a prosthetic device;
    a dynamic interface, capable of changing its geometry, disposed on the surface of the frame, the dynamic interface having a residuum contact surface and at least one actuator adapted to move the residuum contact surface relative to the surface of the frame;
    a control system operably connected to the dynamic interface by at least one connector; and
    at least one perfusion sensor disposed on the dynamic interface and in communication with the control system for providing feedback signals to the control system;
    wherein the control system controls actuation of the at least one actuator; and
    wherein the at least one actuator includes a lateral stabilization system allowing movement of the residuum contact surface in a first direction relative to the surface of the frame while preventing movement in at least a second direction perpendicular to the first direction.

5. The dynamic support apparatus according to claim 2 further comprising wherein the at least one sensor is disposed on a prosthetic device.

6. The dynamic support apparatus according to claim 5 further comprising wherein the at least one sensor is a force sensor.

7. The dynamic support apparatus according to claim 5 further comprising wherein the at least one sensor is a compliance sensor.

8. The dynamic support apparatus according to claim 1 further comprising wherein the control system includes at least one carbon dioxide cartridge for actuating the at least one actuator.

9. The dynamic support apparatus according to claim 1 further comprising wherein the at least one actuator is a bladder.

10. The dynamic support apparatus according to claim 9 further comprising wherein the bladder has an accordion sidewall to increase an actuation distance of the actuator.

11. The dynamic support apparatus according to claim 9 further comprising wherein the lateral stabilization system includes a base plate and a cover plate pivotally coupled by a linkage with the bladder disposed between the base plate and the cover plate and connected thereto.

12. The dynamic support apparatus according to claim 11 further comprising wherein the lateral stabilization system additionally comprises a resilient member connecting the cover plate to the base plate and applying a compressive force therebetween.

13. The dynamic support apparatus according to claim 11 wherein the residuum contact surface is contoured to have rounded corners; and
wherein the cover plate includes the contoured residuum contact surface.

14. The dynamic support apparatus according to claim 9 further comprising wherein the lateral stabilization system includes a base plate pivotally coupled to the frame by a linkage with the bladder disposed between the base plate and the frame and connected thereto.

15. The dynamic support apparatus according to claim 9 further comprising wherein the lateral stabilization system includes a four bar linkage.

16. A dynamic support system comprising:
a frame having a surface, the frame configured to attach to a prosthetic device;
a dynamic interface, capable of changing its geometry, disposed on the surface of the frame, the dynamic interface having a residuum contact surface and at least one actuator adapted to move the residuum contact surface relative to the surface of the frame; and
a control system operably connected to the dynamic interface by at least one connector, the control system configured to receive signals from the prosthetic device;
wherein the control system controls actuation of the at least one actuator; and
wherein the at least one actuator includes a lateral stabilization system allowing movement of the residuum contact surface in a first direction relative to the surface of the frame while preventing movement in at least a second direction perpendicular to the first direction.

17. The dynamic support system according to claim 16 further comprising at least one sensor on the prosthetic device.

18. The dynamic support system according to claim 16 wherein the control system is configured to receive function signals from the prosthetic device.

19. The dynamic support system according to claim 18 wherein the function signals comprising indication of a mode of operation of the prosthetic device.

20. The dynamic support system according to claim 18 wherein the function signals comprising an indication of a current position of the prosthetic device.

21. The dynamic support system according to claim 18 wherein the function signals comprising an indication of load indicative of the loading of the prosthetic device.

* * * * *